US006342208B1

(12) United States Patent
Hyldgaard et al.

(10) Patent No.: US 6,342,208 B1
(45) Date of Patent: Jan. 29, 2002

(54) OIL-IN-WATER EMULSION CONTAINING $C_{10}$-$C_{24}$ FATTY ACID DERIVATIVES FOR TREATING SKIN OF MAMMALS

(75) Inventors: Jorgen Hyldgaard; Jimmi Larsen; Anette Severin Jensen, all of Assens (DK)

(73) Assignee: Plum Kerni Produktion A/S, Assens (DK)

( * ) Notice: Subject to any disclaimer, the term of this patent is extended or adjusted under 35 U.S.C. 154(b) by 0 days.

(21) Appl. No.: 09/230,777

(22) PCT Filed: Aug. 1, 1997

(86) PCT No.: PCT/DK97/00324

§ 371 Date: Mar. 8, 1999

§ 102(e) Date: Mar. 8, 1999

(87) PCT Pub. No.: WO98/05294

PCT Pub. Date: Feb. 12, 1998

(30) Foreign Application Priority Data

Aug. 2, 1996 (DK) .............................. 0828-96
Dec. 20, 1996 (DK) .............................. 1465/96

(51) Int. Cl.$^7$ .............................. A61K 7/42; A61K 7/08; A61K 9/00; A61K 35/78
(52) U.S. Cl. ..................... 424/59; 424/400; 424/725; 424/70.22
(58) Field of Search .............................. 424/195.1, 400, 424/70.22, 725, 59

(56) References Cited

U.S. PATENT DOCUMENTS

| | | | |
|---|---|---|---|
| 4,668,505 A | * 5/1987 | Grollier et al. | 424/47 |
| 5,023,312 A | 6/1991 | Erickson et al. | 558/160 |
| 5,382,381 A | 1/1995 | Imperante et al. | 252/312 |
| 5,518,647 A | * 5/1996 | Zocchi | 252/174.17 |
| 5,654,341 A | * 8/1997 | Struewing | 514/642 |

FOREIGN PATENT DOCUMENTS

| | | |
|---|---|---|
| EP | 0 328 355 A2 | 8/1989 |
| WO | WO 93/21293 | 10/1993 |
| WO | WO 95/17163 | 6/1995 |
| WO | WO 96/32092 | 10/1996 |

OTHER PUBLICATIONS

Barton, A.F.M., "CRC Handbook of Solubility Parameters and Other Cohesion Parameters", CRC Press Inc., Florida, pp. 2–7.

Hannuksela et al., "Irritant effects of a detergent in wash and chamber tests"; *Contact Dermatitis*, vol. 32, pp. 163–166; 1995.

Loden, M., "Biophysical methods of providing objective documentation of the effects of moisturizing creams", *Skin Reasearch and Technology*, vol. 1, pp. 101–108; 1995.

Paye et al., "Corneometry measurements to evaluate skin dryness in the modified soap chamber test", *Skin Research and Technology*; vol. 1, pp. 123–127; 1995.

Serup, J., "EEMCO guidance for the assessment of dry skin (xerosis) and ichthyosis: clinical scoring systems", *Skin Research and Technology*, vol. 1; pp. 109–114; 1995.

Shell Chemicals: Technical Bulletin ICS (x) 75/1.

Hansen, C., "The Absorption of Liquids into the Skin", UDK No. 66.062, publ. Scandinavian Paint and Printing Ink Research Institute.

JP Abstract, publ. No. 58144311, publ. date: Aug. 27, 1983; Nikko Kemikaruzu KK.

JP Abstract, publ. No. 01153623, publ. date: Jun. 15, 1989; Tsumura & Co.

JP Abstract, publ. No. 62153208, publ. date: Jul. 08, 1987; Kawaken Fine Chem Co. Ltd.

Derwent Abatracts of EP 0111895, Henkel KGAA; EP 0643960, Rocher Yves Biolog Vegetable; EP 0145607, L'Oreal; EP 0628305, L'Oreal; and FR 2676645, Sederma (SA).

\* cited by examiner

*Primary Examiner*—David M. Naff
*Assistant Examiner*—Mike Meller
(74) *Attorney, Agent, or Firm*—Peter F. Corless; Christine C. O'Day; Edwards & Angell, LLP

(57) ABSTRACT

An oil-in-water emulsion for application on a skin surface is disclosed. The emulsion comprises an oily phase and an aqueous phase. The oily phase comprises a first lipid of vegetable or animal origin. The emulsion is stabilized by containing at least one surfactant/emulsifier. The surfactant/emulsifier is substantially removed from a skin surface onto which the emulsion has been applied and from the emulsion by flushing with a liquid, thereby leaving at least a part of the oily phase on the skin. When the emulsion is diluted with tap water, which has a degree of hardness of about 18 degrees in a volume of 100 parts of water to one part of the emulsion at ambient temperature, it is separated into at least two distinct phases after standing for 24 hours at ambient temperature. The emulsion has a pH value of at least about 6 and at least about 50% w/w of the total concentration of the surfactant/emulsifier which is a fatty acid derivative. The fatty acid derivative has a fatty acid component which is a saturated or unsaturated $C_{10}$–$C_{24}$ hydrocarbon carboxylic acid or mixtures thereof. The emulsion can be used in a method for cleansing or conditioning a skin surface, for treating human skin, for treating mammals against parasites belonging to the phylum Arthropoda and for protecting human skin against the sun.

32 Claims, No Drawings

OIL-IN-WATER EMULSION CONTAINING $C_{10}$-$C_{24}$ FATTY ACID DERIVATIVES FOR TREATING SKIN OF MAMMALS

BACKGROUND OF THE INVENTION

1. Field of the Invention

The invention relates to an oil-in-water emulsion, especially for use on mammalian skin, in particular on human skin, or hair in order to cleanse the skin or hair, remove dirt, etc., and/or to preserve or improve the condition of the skin, and/or to prevent or treat various skin conditions such as, e.g., dry skin, irritated skin or otherwise traumatized skin. Upon application on a skin surface and following rinsing or flushing the skin surface with a liquid, the oil-in-water emulsion separates into at least two distinct phases and leaves a protective layer on the skin comprising at least a part of the oily phase.

An oil-in-water emulsion according to the invention also has useful properties with respect to protection of the skin against sun light and with respect to combatting attack from parasites like lice, fleas and scabies on mammals such as humans, domestic animals and pets. Thus, in other aspects of the invention it relates to a method for combatting attack from such parasites by administering an effective amount of an oil-in-water emulsion.

In other aspects the invention relates to a method for cleansing, conditioning or treating the skin by application of an oil-in-water emulsion. Furthermore, the invention relates to a skin-friendly lipid, namely Meadowfoam seed oil, as a therapeutic agent, and as an agent which in itself in synergistic effect with other constituents is effective against mammalian parasites, especially from the phylum Arthropoda, and as an agent which is effective as a sun screen or a UV-A, UV-B or UV-C filter.

2. Description of Related Art

In many industrial activities and during household chores, it is necessary for people to expose their skin, and especially their hands and arms, to environments wherein their skin especially on arms and/or hands may become soiled, stained or injured by mechanical or chemical exposure, or the like. Furthermore, many industrial activities and household chores require a high hygienic standard, particularly in the food and medicinal industries and in hospitals.

A high hygienic standard comprises a very frequent exposure of human skin to cleansing involving various kinds of soaps and other chemicals in order to disinfect the skin and/or to remove soil and unwanted microorganisms, especially pathogenic microorganisms, from the skin surface.

The skin may be cleansed with detergents, solvents or abrasives, singly or in combination. Among the detergents, soaps have enjoyed the greatest official status. The non-soap detergents have become important, not only as household cleansers but also in industry and in dermatologic and surgical practice as well.

Most persons who frequently wash and clean their skin, especially on their hands, very often develop a dry skin surface and, furthermore, the skin becomes irritated and rough, most likely because the barrier function of the skin is negatively affected by the compositions used for cleansing and washing the skin.

Despite of many years of research within the personal cleansing field, the majority of the consumers finds that the present day cleansing compositions still need improvement with respect to a gentle and mild cleansing of the skin. Thus, the consumers normally find it necessary to apply a separate lotion or creme to the skin after using a cleansing product (industrial use as well as general use in the household in the form of e.g. shower or bath preparations) in order to counteract the delipidizing and demoisturizing effect of the cleanser.

Such lotions or cremes are generally in the form of emulsions such as a an oil-in-water emulsion, i.e. with a content of tensides, surfactants or emulsifiers in order to avoid leaving a greasy feeling upon application onto the skin and thereby improve user acceptance. The lotions or cremes are rubbed into the skin leaving the ingredients, including the tensides, surfactants or emulsifiers, as a deposit on the surface of the skin. However, tensides, surfactants and/or emulsifying agents are generally believed to be irritative to the skin which in turn means that it would be highly desirable to avoid a deposit of such agents on the skin surface after application of a topical composition (such as, e.g., a cleansing composition, a lotion, a creme, etc.). A tenside deposited on the skin is believed to partly dissolve the lipids within the skin; the lipids will then be removed from the skin e.g. by washing or sweating often resulting in the development of dry skin.

In general, cleansing compositions in the form of oil-in-water emulsions are preferred because they have a non-greasy and clean feel. However, a problem with the present day cleansing compositions is that effective personal cleansing compositions are difficult to formulate as an oil-in-water emulsion due to the fact that a surfactant/emulsifier is incorporated in the oil-in-water emulsion for storage stability reasons (i.e. to avoid phase separation during storage). The requirement of having a good storage stability is, however, a drawback with regard to the cleansing ability of the emulsion if the oil phase is held too tightly to the aqueous phase and therefore does not become available during the cleansing process. Furthermore, surfactants/emulsifiers which are added to the emulsion due to their cleansing abilities can also reduce the cleansing effect of the emulsion because the surfactant/emulsifier retains its effect as an emulsifier and thereby renders both the cleansing active surfactant/emulsifier and the oil phase less available for cleansing.

Furthermore, with a view to the environment, there is a growing demand for a general use of ingredients which are friendly to the environment, i.e. ingredients which can be degraded or decomposed by nature or otherwise degraded into harmless substances.

International patent application published under No. WO 96/32092 (The Procter & Gamble Company) on Oct. 17, 1996, i.e. after the priority date of the present application, relates to personal cleansing compositions comprising acrylic salts or derivatives of acrylic acid.

U.S. Pat. No. 5,382,381 (Imperante et al.) relates to emulsions comprising silicone bases phosphate esters.

International patent application published under No. 95/17163 (Colgate-Palmolive Company) relates to a skin cleansing composition comprising a combination of a high-foaming and a mild-foaming substance.

European patent application published under No. 0 111 895 (Henkel Kommanditgesellschaft auf Aktien) relates to a skin conditioning composition in the form of an emulsion. The oily component contains as mandatory constituents paraffin oil or silicon oil or a mixture thereof.

SUMMARY OF THE INVENTION

As will be apparent from the above, there is a need for the development of improved cosmetically acceptable compositions which can be used for cleansing a skin surface. The present invention relates to such improved cosmetically acceptable compositions which can be used for cleansing a skin surface, especially a human skin surface, and which contain ingredients which are safe for the environment, i.e. ingredients which in sewage disposal plants are decomposed into substantially harmless substances, and which have a protective effect on the skin (e.g. against irritation and drying), and which have an emollient effect, and which have excellent cosmetic and physical stability, and which are capable of leaving at least a part of the oil phase on the skin upon cleansing or washing the skin surface with the composition and rinsing or flushing the skin surface with a suitable liquid; the part of the oil phase remaining on the skin surface after use of the composition imparts conditioning, smoothing and emollient properties to the skin and, thus, reduces the tendency to develop dry, irritated or otherwise traumatized skin.

As it is discussed in detail below the skin-friendly effect of a composition according to the present invention is so advantageous that in many cases cleansing of the skin need not be followed by application of a moisturizing or otherwise skin conditioning conventional lotion or creme in order to preserve the skin surface substantially intact and untraumatized.

The novel personal cleansing compositions are in the form of oil-in-water emulsions. Even when a natural soap is contained in the emulsions, they are surprisingly storage stable, yet have a suitable low viscosity. Furthermore, the emulsions are easily spread on the skin, easy to dilute and to remove from the skin and to separate into two distinct phases. The emulsions also exhibit excellent mildness and cleansing effect and at the same time significantly minimize a delipidizing effect on the skin; on the contrary—and as is explained in further detail in the examples given herein—an emulsion according to the present invention provides a deposit of a lipid on the skin and, accordingly, it preserves the normal barrier function of the skin. Furthermore, the oil-in-water emulsions have an excellent ability of breaking into an oily and an aqueous phase upon dilution or rinsing with a suitable flushing medium such as, e.g., plain water while at the same time exerting an excellent storage stability.

Thus, in one aspect the present invention relates to an oil-in-water emulsion for application on a skin surface, the emulsion comprising a skin-friendly oily phase and an aqueous phase, the emulsion being stabilized by containing at least one surfactant/emulsifier, the at least one surfactant/emulsifier being capable of being substantially removed from a skin surface onto which the emulsion has been applied and from the emulsion by flushing with a liquid, thereby leaving at least a part of the oily phase on the skin, and the emulsion—when diluted with tap water having a degree of hardness of about 18 degrees in a volume of 100 parts of water to one part of the emulsion at ambient temperature—being separated into at least two distinct phases after standing for 24 hours at ambient temperature.

As mentioned above, an oil4n-water emulsion according to the invention leaves at least a part of the oily phase on the skin upon cleansing the skin with the oil-in-water emulsion. The at least one part of the oily phase which remains on the skin surface covers the skin surface with a thin layer acting as a protective layer against drying of the skin. The thin layer of the at least one part of the oily phase also has a smoothing and/or emollient effect on the skin (discussed in further detail below).

Therefore, an oil-in-water emulsion according to the invention is especially suitable for use by persons who frequently wash or clean their skin, such as the skin on their hands or arms, for persons whose skin surface is exposed to chemical or mechanical influences, for persons whose skin surface or part of the skin surface becomes soiled e.g. by greasy substances during work, or for persons who suffer from dry skin or irritated skin.

Research has shown that when conventional washing or cleansing soaps are substituted with an emulsion according to the invention then the following normal feeling of dry skin is avoided, thus reducing or even eliminating the need for using a conditioning lotion or creme.

In general, all persons who—after washing or cleansing of the skin—find it necessary to apply a lotion, creme, or the like with some conditioning effect on the skin can advantageously make use of an emulsion according to the invention.

The skin surface onto which an oil-in-water emulsion according to the invention is applied is a mammal skin surface, especially a human skin surface. In the present context the term "skin surface" relates to the outermost surface of the body and embraces intact skin as well as injured skin surfaces, mucosa and mucous membranes. The term "skin surface" is used in a very broad sense embracing the epidermal layer of the skin and—in those cases where the skin surface may be injured—also the dermal layer of the skin. The epidermal layer of the skin is the outer (epithelial) layer and the deeper connective tissue layer of the skin is called the dermis. The skin may have a thick or a thin epidermis and is therefore often classified as thick or thin skin. In the present context, the term "skin" embraces thick skin as well as thin skin.

Thick skin is found on the palms of the hands and the soles of the feet, whereas thin skin covers the remainder of the body. The skin on the palms of the hands and the soles of the feet has a thick epidermis with a particularly thick layer of keratin on its outer surface. The skin covering the remainder of the body has a relatively thin epidermis and the outer keratinized layer of the epidermis is relatively thin.

DETAILED DESCRIPTION OF THE INVENTION

As mentioned above, an emulsion according to the invention separates into at least two distinct phases when the emulsion applied on the skin is flushed with a liquid. In principle the flushing medium can be any suitable liquid provided that it has the ability to impart a separation of the emulsion into distinct phases. The separation of the emulsion into at least one oily phase and at least one aqueous phase means that the function of at least a part of the stability-imparting substance/substances present in the emulsion is destroyed. Therefore, the type of liquid used as the flushing medium depends on the ingredients contained in the emulsion. In general, tap water with a degree of hardness of about 8–25 degrees, such as about 15–25 degrees such as e.g. 18 degrees, is suitable as flushing medium, but suitable liquids may also be other kinds of aqueous solutions comprising e.g. alcohols like ethanol, propanol, and isopropyl alcohol, salts, etc. The term "tap water" when used herein is water having a content of $Ca^{++}$ and $Mg^{++}$ ions (which ions can form insoluble salts with fatty acids) and resulting in a degree of hardness of about 8–25 degrees, such as about 15–25 degrees such as e.g. 18 degrees.

In order to be a suitable flushing medium, the liquid should be able to destroy or otherwise negatively influence the function of the surfactant/emulsifier present in the emulsion, either by destroying the surfactant/emulsifier in itself or by being able to establish a binding to the surfactant/emulsifier which binding is stronger than the binding between the surfactant/emulsifier and the oily phase. In the first case, where the surfactant/emulsifier is destroyed or the function of the surfactant/emulsifier is otherwise negatively influenced, the function of the surfactant/emulsifier can be destroyed e.g. by adding a liquid having a content of ions or other substances which are capable of forming substantially insoluble salts with the surfactant/emulsifier present in the emulsion. Examples of such ions are e.g. $Ca^{++}$, $Mg^{++}$, etc. The function of the surfactant/emulsifier may also be destroyed due to a dilution of an additive in the emulsion leading to a degradation of the surfactant/emulsifier. For the purpose of the present invention it is believed that at least about 30% w/w such as at least about 50% w/w of the content of the surfactant/emulsifier should be destroyed by rinsing with a flushing medium.

As will be discussed in detail below and in the examples herein it is contemplated that the presence of an excess of free fatty acid in an oil-in-water emulsion according to the invention contributes to an easy breaking of the emulsion when the emulsion is contacted with a suitable flushing medium. In those cases, where no or only an insufficient amount of free fatty acid is present in an emulsion according to the invention it is therefore envisaged to obtain the same easiness in breaking the emulsion by adding a suitable amount of free fatty acid (or any other cosmetically acceptable acid) to the flushing medium. Other appropriate ingredients may of course also be added to the flushing medium in order to impart the breaking of the emulsion (e.g. salts like $Ca^{2+}$ or $Mg^{2+}$ salts) or to obtain a beneficial effect on the skin (e.g. conditioners, flocculating agents etc.).

The suitability of a specific liquid for use as a flushing medium can be determined e.g. by dilution of an emulsion according to the invention with the specific liquid in a volume of e.g. 100 parts of water to 1 part of the emulsion (this ratio seems to be closest to the ratio obtained in practice). However, other ratios may also be relevant, such as e.g. a ratio of 10:1 or 4:1 at ambient temperature. If the emulsion has separated into at least two distinct phases after being allowed to stand for 24 hours at ambient temperature, then the liquid might be suitable for use as a flushing medium provided that other requirements are also fulfilled (such as e.g. a skin-friendly nature of the liquid).

Skin-friendly First Lipid

The at least one part of the oily phase which remains on the skin after flushing with a liquid comprises a skin-friendly first lipid. The lipid is present in the emulsion in a concentration corresponding to at least about 1% w/w, such as e.g. at least about 2% w/w, at least about 3% w/w, at least about 4% w/w, at least about 5% w/w based on the total emulsion, or corresponding to a range of from about 1–50% w/w such as e.g. about 2–40% w/w, about 2–35% w/w, about 2–30% w/w based on the total emulsion. The lipid may also be effective even in concentrations below about 4% w/w.

A lipid suitable for use according to the above is a lipid which has a good adherence to the skin. A good adherence to the skin can be evidenced objectively by persons applying the lipid to the skin or, alternatively, by use of standardized methods for the evaluation of bioadhesion. Furthermore, a lipid suitable for use according to the invention is a lipid which is liquid or semi-solid or solid (such as e.g. lanolin) at room temperature. In some cases a lipid in liquid form is found to be the most suitable.

Other lipids which are suitable for use as a first lipid in an emulsion according to the invention are lipids which have such a water retention ability that 1 g of the lipid can retain at least 2 g of water at ambient temperature. Relevant examples of such lipids are Meadowfoam seed oil, Shea butter (Karite butter), cocoa butter, lanolin, and mixtures thereof. Meadowfoam seed oil can retain 6 times its own weight of water and a mixture of Meadowfoam seed oil and Karite extract (available under the name FANCOL VB from Fanning Corporation, U.S.A.) can retain about 8 times its own weight of water.

The water retention ability is believed to be important in order i) to supply moisture to the skin onto which the emulsion has been applied, and ii) to enable application of e.g. moisture absorbing or adjusting agents (e.g. urea or urea derivatives which have been dissolved or suspended in the oily phase of the emulsion).

Apart from the above-mentioned advantages with respect to the moisture regulation of the skin, the function of the skin-friendly first lipid alone or in combination with other constituents of the oily phase of the emulsion is:
  i) to enable application of oil-soluble vitamins to the skin (e.g. by dissolving the vitamin(s) in question in the oily phase of the emulsion), and
  ii) to protect the barrier of the skin or to contribute to a recovery of the skin barrier (e.g. expressed by measuring the transepidermal water loss (TEWL) as explained in the examples herein).

Furthermore, a useful effect has been observed with respect to exerting an effect against sun light and—when applied to or on hair—against parasites from the phylum Arthropoda (e.g. lice, fleas, scabies, etc.), i.e. the first lipid may in itself or in combination with other constituents of the oily phase of the emulsion be a UV-filter or a sun screen.

Furthermore, a deposit of a lipid on the skin (or hair) after application is very advantageous because the property of an emulsion according to the invention can be further utilized by adding active agents to an emulsion or oily phase of an emulsion according to the invention. The active agent to be added must have a certain solubility in the oily phase or it may suspended in the oily phase in order to ensure that the agent is delivered to the skin or hair surface. Relevant active agents are e.g. i) agents which protect against sun light, ii) agents which protect against external microorganisms, iii) agents which protect against oxygen, agents which protect against aggressive substances (e.g. substances in the atmospheric air, liquids and solids), iv) agents which are effective against e.g. lice, v) drug substances, and vi) agents which have a conditioning or emollient or otherwise beneficial effect on the skin.

A lipid which has proved suitable for use in the present context is a lipid which is a triglyceride comprising at least 90% of long chain $C_{20}$–$C_{22}$ fatty acids.

The long chain $C_{20}$–$C_{22}$ fatty acids may be saturated or unsaturated (mono-, di-, or triunsaturated) fatty acids.

A triglyceride comprising a combination of a monoenoic and a dienoic fatty acid component has especially proved to be suitable for the intended use. In the combination, the ratio of the monoenoic fatty acid component to the dieonic fatty acid component is in a range corresponding to from about 1:99 to about 99:1 such as e.g. from about 1:50 to about 50:1, from about 1:26 to about 25:1, from about 1:10 to about 10:1 such as about 3:1 to about 6:1.

In a useful combination, the two unsaturated bonds of the dienoic fatty acid component is spaced from each other by at least 3 carbon atoms, such as at least 5, 6, 7, 8 or 9 carbon atoms.

A specific lipid which has proved suitable for use and which is also skin-friendly is triglycerides derived from plant species of the family Limnanthaceae such as *Limnanthes alba*. Meadowfoam seed oil is an example of such a lipid.

Meadowfoam seed oil—also denoted Meadowfoam triglyceride—is very stable towards oxidation and heat. It comprises triglycerides about 96% of which are long chain $C_{20}$–$C_{22}$ fatty acids. The composition of Meadowfoam triglyceride is:

Long chain $C_{20}$–$C_{22}$ fatty acids: 95–97%, and the approximate content of long chain fatty acids are:

| | |
|---|---|
| 20:0 (i.e. a $C_{20}$ fatty acid having 0 double bonds) | 0.05 |
| 20:1 (delta 5) (i.e. a $C_{20}$ fatty acid having 1 double bond at the 5 position) | 62.5 |
| 20:1 (delta 13) | — |
| 22:1 (delta 5) | 2.5 |
| 22:1 (delta 13) | 12 |
| 22:2 (delta 5, delta 13) | 18 |
| Other (primarily $C_{18}$ tocopherols) | 0.5 |

As mentioned above other specific interesting lipids for use as a first lipid in an emulsion according to the invention are lanolin, cocoa butter and shea butter (Karite extract). In the following is given the composition of cocoa butter and shea butter, respectively.

| Chemical constituents of shea butter and cocoa butter | | |
|---|---|---|
| Fatty acid (WL %) | Cocoa butter | Shea butter |
| Palmitic | 24.4 | 5.7 |
| Stearic | 35.4 | 41.0 |
| Arachidic | 0 | 0 |
| Total saturated | 59.8 | 46.7 |
| Oleic | 38.1 | 49.0 |
| Linoleic | 2.1 | 4.3 |
| Total unsaturated | 40.2 | 53.3 |
| Glycerides (mole %) | | |
| Triunsaturated | 2.5 | 5.0 |
| Monounsaturated Palmitostearin | 52.0 | — |
| Monounsaturated Dipalmitin | 8.5 | — |
| Monounsaturates Distearin | 18.4 | 34.0 |
| Diunsaturated stearin | 12.0 | 45.0 |
| Diumsaturated palmitin | 8.4 | 11.0 |
| Triunsaturated | 0 | 5.0 |

| Physical constants of shea butter and cocoa butter | | | |
|---|---|---|---|
| Parameter | Cocoa butter | Shea butter | Refractive index |
| (40° C.) | 1.44–1.45 | 1.46 | |
| Acid value | 1–4 | 2.2 | |
| Iodine value | 34–38 | 48–60 | |
| Saponification value | 200–240 | 160–180 | |
| Melting point (° C.) | 35 | 37–38 | |
| Polymorphic forms | = 4 | 2 | |
| Colour | Golden Yellow | Straw | |
| Odour | Like chocolate | Characteristic fatty smell | |
| Feel | Slightly greasy | Sligtly greasy | |
| Specific gravity (20° C.) | 0.856–0.864 | 0.91–0.95 | |
| Percent of unsaponifiables | 0.2–1.0 | 3–13 | |

The present inventors have also found that beneficial effects are obtained when a first lipid is mixed with a vegetable extract such as, e.g. Karite butter extract and/or Karite extract. However, other extracts are also believed to be useful in the present context e.g. extracts such as, e.g., aloe barbadensis extract, apricot extract, arnica montana extract, balm mint extract, bamboo extract, bearberry extract, beet extract, bilberry extract, birch leaf extract, blackberry leaf extract, bladderwrack extract, buckwheat extract, burdock extract, butcherbroom extract, calendula extract, carrot extract, matricaria extract, cherimoya extract, jujube extract, coltsfoot extract, comfrey extract, coneflower extract balsam copaiba, cornflower extract, cucumber extract, dog rose hips extract, fennel extract ginger extract, ginkgo extract, ginseng extract, camellia sinensis extract, guarana extract, crataegus monogina extract, hayflower extract, henna extract, hops extract, horsetail extract, horsechestnut extract, hydrocotyl extract, ivy extract, Job's tears extract, juniperus communis extract, kiwi extract, lady's mantle extract, laminaria digitata extract, lavender extract, lemon peel extract, licorice extract, linden extract, lithospermum officinale extract, mallow extract, mango extract, marshmallow extract, melon extract, mimosa tenuiflora bark extract, white oak bark extract, English oak extract, oyster shell extract, pansy extract, peach extract, capsicum frutescens oleoresin, capsicum frutescens extract, peppermint extract, quillaja saponaria extract, raspberry extract, krameria triandra extract, rosemary extract, sage extract, St. John's wort extract, stinging nettle extract, strawberry extract, soapwort extract, thyme extract, walnut extract, watercress extract, wheat germ extract, willow bark extract, witch hazel extract.

With respect to the concentration of the first lipid, or whenever relevant in combination with an extract, in the emulsion, it is generally in a range corresponding to from about 1% to about 50% w/w such as, e.g., from about 2 to about 30% w/w, from about 1 to about 20, from about 2 to about 10.

Instead of using a lipid or mixtures of lipids in order to form a protective layer on the skin surface, a protein or a proteinaceous substance may be used either alone or in admixture or in combination with a lipid. Vegetable protein hydrolysates (such as e.g. hydrolyzed wheat gluten (Gluadin, Tritisol), almond flour hydrolysate (Gluadin Almond)), wheat protein fatty acid condensates (such as e.g. sodium cocoyl hydrolyzed wheat protein (Gluadin WK)) and cationic wheat protein hydrolysates (such as e.g. laurdimonium hydroxypropyl hydrolyzed wheat protein (Gluadin WQ)) are considered suitable for use in an emulsion according to the present invention. Furthermore, suitable vegetable proteins may be soybean, pea and rice protein as well as almond flour.

Surfactant/emulsifier

An emulsion according to the invention contains at least one surfactant/emulsifier. Especially in oil-in-water emulsions intended for cleansing purposes, the at least one surfactant/emulsifier plays an active role in the cleansing process, i.e. it has a cleansing ability in itself. Furthermore, the surfactant/emulsifier imparts physical stabilization to the emulsion so that it has an excellent storage stability.

In the present context the terms "surfactant", "surface active agent" and "tenside" are used to denote a substance that reduces surface tension when dissolved in water or aqueous solutions, or which reduces interfacial tension between two liquids, or between a liquid and a solid. Three categories of surface active agents are: detergents, wetting agents, and emulsifiers.

The term "detergent" is generally defined as a substance that reduces the surface tension of water; specifically a surface active agent which concentrates at oil-water interfaces, exerts emulsifying action, and thus aids in removing soils. The older and still widely used types are the common sodium and potassium soaps of fatty acids (classified as anionic surfactants). The synthetic detergents are classified as anionic, cationic, nonionic, or amphoteric depending on their mode of chemical action.

The term "wetting agent" is generally defined as a substance which, when added to water, causes it to penetrate more easily into, or to spread over the surface of, another material by reducing the surface tension of the water.

The term "emulsifier" is generally defined as a substance that is capable of lowering the interfacial tension between an oil and an aqueous phase and, thus, aids the dispersal of oil (in the case of oil-in-water emulsions) and water (in the case of water-in-oil emulsions), respectively, into droplets of a small size and helps to maintain the particles in a dispersed state. Emulsifiers are generally classified as i) proteins or carbohydrate polymers, which act by coating the surface of the dispersed fat or oil particles, thus preventing them from coalescing; such emulsifiers are sometimes also called protective colloids, and ii) long-chain alcohols and fatty acids, which are able to reduce the surface tension at the interface of the suspended particles because of the solubility properties of their molecules. Soaps behave in this manner, they exert cleaning action by emulsifying the oily components of soils.

The term "soap" generally covers two types, namely i) a water-soluble reaction product of a fatty acid ester and an alkali (such as e.g. sodium hydroxide) with glycerol as by-product (a soap is actually a specific type of salt, the hydrogen of the fatty acid being replaced by a metal, which in ordinary soaps is usually sodium; soap lowers the surface tension of water and thus permits emulsification of fat-bearing soil particles; a typical soap is made by reacting sodium hydroxide with a fatty acid), and ii) heavy-metal soaps which are formed by metals heavier than sodium (aluminium, calcium, magnesium, cobalt, lead, zinc, etc.) Heavy-metal soaps are insoluble in water.

In the present context, the term surfactant/emulsifier is used in the meaning of the above-given definitions of "a surface active agent", "a surfactant", "a detergent", "a wetting agent", "an emulsifier", "a soap", and/or "a tenside".

A suitable surfactant/emulsifier for use in an emulsion according to the invention is appropriately a substance which has suitable ecotoxicological properties, i.e. a substance which either in itself or upon degradation is relatively non-toxic. Many non-soap detergents do not decompose in sewage disposal plants. Therefore, the present inventors have focused on developing an emulsion notably a cleansing lotion based on real/natural soaps, i.e. substances which are relatively harmless to the environment. The use of non-soap detergents makes it possible to prepare compositions having a pH value near the pH value of the skin (i.e. a pH about 5–5.5) whereas the presence of natural soaps in a composition normally leads to a resulting pH of the composition to a value of at least 6, i.e. a pH which has been considered as highly unsuitable. However, the importance of a pH about skin pH has been overrated and in connection with the present invention and as shown in the Examples herein, the present inventors have shown that compositions having a higher pH than that of the skin are well-tolerated on the skin and, furthermore, impart conditioning of the skin. Suitable pH values for the latter compositions are in a range from about 6 to about 8.6 or to about 9 such as, e.g., from about 6 to about 8, from about 7 to about 8, or from about 7.2 to about 7.8.

As discussed earlier, the presence of an excess of free fatty acid in the emulsion seems to have a positive impact on the ability of the emulsion to break. The pH should therefore be at the most about 8.6–9 such as about 8.6 to about 8.8 (corresponding to an emulsion wherein no free fatty acid is present), preferably at the most 8 such as stated above.

Suitable surfactants/emulsifiers for use in an emulsion according to the invention are fatty acid derivatives especially fatty acids which are neutralized to form a soap. Suitable surfactants are found among anionic and non-ionic soaps. Preferably, the surfactants/emulsifiers possess good emulsifying properties. Examples of suitable fatty acid derivatives are sodium salts, potassium salts, ammonium salts, substituted ammonium salts, unsubstituted amides, amides with substituted amines including ethanolamides (such as monoethanolamides, diethanolamides and triethanolamides), propanolamides, isopropanolamides, and mixtures thereof.

The fatty acid component of the fatty acid derivative for use in an emulsion according to the invention is typically a saturated or unsaturated $C_{10}$–$C_{24}$ hydrocarbon carboxylic acid, or mixtures thereof.

Examples of suitable saturated fatty acids are e.g. capric acid ($C_{10}H_{20}O_2$), undecylenic acid ($C_{11}H_{22}O_2$) lauric acid ($C_{12}H_{24}O_2$), myristic acid ($C_{14}H_{28}O_2$), palmitic acid ($C_{16}H_{44}O_2$), stearic acid ($C_{18}H_{36}O_2$), arachidic acid ($C_{20}H_{40}O_2$), behenic acid ($C_{22}H_{44}O_2$), and lignoceric acid ($C_{24}H_{48}O_2$), and mixtures thereof.

Examples of suitable mono-unsaturated fatty acids are palmitoleic acid ($C_{16}H_{30}O_2$), oleic acid ($C_{18}H_{34}O_2$), ebidic acid ($C_{18}H_{34}O_2$), erucic acid ($C_{22}H_{42}O_2$), and brassidic acid ($C_{22}H_{42}O_2$), and mixtures thereof.

Examples of suitable di- or triunsaturated fatty acids are linoleic acid ($C_{18}H_{32}O_2$) and linolenic acid ($C_{18}H_{30}O_2$), and mixtures thereof.

The at least one surfactant/emulsifier for use in an emulsion according to the invention may also be a mixture of fatty acid derivatives wherein the fatty acid components are saturated, monounsaturated, diunsaturated or triunsaturated, or mixtures thereof.

The at least one surfactant/emulsifier for use in an emulsion according to the invention can also be an anionic tenside such as a tenside selected from the group consisting of alkyl sulfates, N-acyl glutamates, acyl isethionates, alkyl sulfosuccinates, alkyl phosphate esters, ethoxylated alkyl phosphate esters, trideceth sulfates, protein condensates, mixtures of ethoxylated alkyl sulfates, and mixtures thereof. Combinations of an anionic tenside with a non-ionic soap as those mentioned above are of course also relevant in the present context.

Furthermore, the at least one surfactant/emulsifier for use in an emulsion according to the invention may be an amphoteric tenside such as a tenside selected from the group consisting of sodium 3-dodecylaminopropionate; sodium 3-dodecylaminopropane sulfonate; N-alkyltaurines; betaines including cocoamidopropyl betaine, coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl)carboxymethyl betaine, oleyl dimethyl gamma-carboxypropyl betaine, lauryl bis-(2-hydroxypropyl) alpha-carboxyethyl betaine, coco dimethyl sulfopropyl betaine, stearyl dimethyl sulfopropyl betaine, amido betaines, amidosulfobetaines; 4-[N,N-di(2-hydroxyethyl)-N-octadecyclammonio]-butane-1-carboxylate; 5-[S-3-3 hydroxypropyl-S-hexadecylsulfonio]-3 hydroxypentane-1-sulfate; 2-[P,P,P-diethyl-P 3,6,9 trioxatetradexocyl-phosphonio]-2-hydroxypropane-1-phosphate; 3-[N,N-dipropyl-N-3-dodecoxy-2-hydroxypropylammonio]-propanel-phosphonate; 3-(N,N,-di-methyl-N-hexadecylammonio) propane-1-sulfonate; 3-(N,N-dimethyl-N-hexadecylammonio)-2-hydroxypropane-1-sulfonate; 4-(N, N-di(2-hydroxyethyl)-N-(2 hydroxydodecyl) ammonio)-butane-1-carboxylate; 3-[S-ethyl-S-(3dodecoxy-2-hydroxypropyl)sulfonio]propane-1-phosphate; 3-(P,P-dimethyl-P-dodecylphosphonio)-propane-1-phosphonate; and 5-[N,N-di-(3-hydroxypropyl)-N-hexadecylammonio]-2-hydroxy-pentane-1-sulfate.

Normally, the concentration of the at least one surfactant/emulsifier in the emulsion is in a range corresponding to from about 5 to about 25% w/w such as, e.g., from about 8 to about 20% w/w or from about 10 to about 15% w/w. In the concentrations given, the at least on surfactant/emulsifier is capable of removing dirt from the human skin.

An emulsion according to the invention may also comprise a further surfactant/emulsifier, i.e. a substance which aids in stabilizing the emulsion. Suitable surfactants/emulsifiers have an HLB value in a range corresponding to from about 4 to about 30 such as in a range of from about 6 to about 17.

The total concentration of surfactant/emulsifier in the emulsion is in a range corresponding to from about 5 to about 40% w/w, such as, e.g., from about 10 to about 35% w/w or from about 15% to about 25% w/w.

Examples of suitable surfactants/emulsifiers for use in an emulsion according to the invention are polyoxyethylene sorbitan fatty acid monoesters (e.g. Tween series), polyoxyethylene sorbitan fatty acid triesters (e.g. Tween series), polyoxyethylene alkylphenol ethers (e.g. Triton X-series), polyoxyethylene fatty alcohol ethers (e.g. Cetomacrogol series; Brij series; Renex series), alkyl fatty alcohol ethers (e.g. fatty alcohol ethyl ethers), polyoxyethylene fatty acid esters (e.g. Myrj series), sorbitan fatty acid monoesters (e.g. Arlacel and Span series), sorbitan fatty acid triesters (e.g. Arlacel and Span series), alkyl phosphate esters (e.g. Berol series), fatty acid monoethanol amides, fatty acid diethanol amides, fatty acid amidoalkyl betaines (betaines), fatty acid amidoalkyl sulfobetaines (sulfobetaines), sulfated hydroxyfatty acids (e.g. sulfated castor oil ("Turkish red oil")).

Specific examples of suitable surfactants/emulsifiers indexed after their HLB values are found in McCutcheon's Emulsifiers & Detergents, 1990 International Edition.

Examples of suitable surfactant/emulsifiers for use in an emulsion according to the invention are;
  Cocamide MEA
  Cocamidopropyl betaine
  C9-11 Pareth 6
  Other interesting surfactant/emulsifiers for use in an emulsion according to the invention are:
  Ethoxylated castor oil
  Mono/diglycerides
  Lanolin derived extracts of sterols and sterol esters
  Ester of a polyglycerol derivative
  Decaglycerin pentaoleate
  Glycerol monostearate
  POE (2) monostearate
  Sorbitan trioleate
  Calcium alkylbenzene sulfonate
  Hydroxylated lanolin
  Sorbitan sesquioleate
  Oxyfatty acid monoglyceride
  Polyethylene glycol dodecylphenol ether
  Sorbitan sesquistearate
  Sorbitan monooleate
  Mannide monooleate
  Sorbate 80/sorbitan monooleate
  Ethoxylated polyoxypropylene glycols
  Refined wool fat
  Lanolin and lanolin alcohol
  Sorbitan monostearate
  Nonylphenol ethoxylate
  Glycerol monostearate
  POE (2) monooleate
  Sorbitan monoisostearate
  Sorbitan sesquioleate
  Nonyl phenol ethylene oxide condensate
  Sorbitan ester
  Glycerol palmitic/stearic acid esters
  Glycerol mono/distearate
  Ethoxylated nonylphenol
  POE glycerol sorbitan fatty acid ester
  POE (2) stearyl alcohol
  POE (2) oleyl alcohol
  Polyethoxylated (2) stearyl alcohol
  Polyethoxylated (2) oleyl alcohol
  De-oiled lanolin
  Isobutylated lanolin oil
  Ethoxylated glycerol sorbitan oleostearate
  POE-(6)-sorbitol beeswax derivative
  POE-(20)-sorbitol beeswax derivative
  Lactic acid fatty acid glyceride
  Lactic acid ester of mono/diglycerides
  PEG-7 hydrogenated castor oil
  Diethylene glycol monooleate
  Diethylene glycol monostearate
  POE glycerol triricinoleate
  Methyl glucoside dioleate
  Sorbate 60/sorbitan monostearate
  Diglyceryl monostearate
  Glycerol monostearate
  Sorbitan monoisostearate
  Sorbitan monooleate
  Polyoxyethylene nonylphenyl ether Diethylene glycol monolaurate, SE
Block copolymer of ethylene oxide and propylene oxide
Fatty alcohol ethoxylate
Sucrose fatty acid esters
Methyl glucoside sesquistearate
Polyglyceryl-3 diisostearate
Ethoxylated triglyceride
POE (5) hydrogenated castor oil
Tetraglyceryl monooleate
Tetraglyceryl monostearate
Polyoxyethylene Isoryl ether
Sorbitan monopalmitate
Ethoxylated castor oil
Decaglycerin tristearate
Sorbitan monopalmitate
Polyoxyalkylene glycol
PEG 400 dioleate
PEG (8) distearate
PEG 200 monostearate
PEG 400 distearate
Polyoxyethylene lauryl ether
Polyethylene glycol monostearate
Polyethylene glycol nonylphenol ether Furthermore, the present inventors have observed that a certain content of free fatty acid in the composition (i.e. when a free fatty acid is included in an emulsion of the present invention, it is preferably included in an excessive amount so that when the soap has been formed, then a free amount of free fatty acid is still present in the emulsion) is of importance with respect to the easiness with which the emulsion breaks or separates into at least two distinct phases upon dilution with a suitable flushing medium like e.g. plain water. A measure of the content of fatty acid in an emulsion according to the invention is the acid value. The acid value of an emulsion according to the invention should preferably correspond to a range of from about 10 to about 60 mg KOH/g, such as, e.g., from about 20 to about 55 mg KOH/g, from about 30 to about 45 mg KOH/g, from about 35 to about 40 mg KOH/g or from about 36.0 to about 37.0 mg KOH/g.

With respect to stabilization of the emulsion the use of especially a combination of ricinus oil derivatives have proved to be excellent. A useful combination is e.g. a combination of glycerinmonoricinoleate (available as Rilanit GMRO from Henkel) and a sulfated ricinus oil (available as Ttirkischrotole from Becker Chemie GmbH, Germany).

Oily Phase

The emulsion contains an oily phase. The oily phase may constitute not more than about 50% w/w of the total emulsion such as in a range corresponding to about 1–50% w/w such as about 5–40% w/w, and about 10–30% w/w.

The functions of the oily phase and/or its individual constituents are i) to serve as the disperse phase in an emulsion according to the invention, ii) to contribute to a cleansing effect of an emulsion according to the invention (the oily phase or its constituents can solubilize, bind and/or emulsify oily dirt etc. e.g. present on the skin and, accordingly, such oily dirt which notably is soluble in oil or lipid is easily cleansed), iii) together with the aqueous phase—to contribute to a suitable viscosity of an emulsion according to the invention without decreasing the storage stability of the emulsion, iv) to contribute to removal of unwanted microorganisms from the skin (or hair), and v) to contribute to removal of unwanted other substances from the skin or the hair such as, e.g., particles, solids, parasites.

Furthermore, the oily phase and/or its constituents contribute to a deposit of a part of the oily phase on the skin (or hair) after application of an emulsion according to the invention. As discussed above suitable agents may be incorporated in the oily phase (or in the emulsion) in order to enable application of the agent(s) to the skin (or hair). Such agents are e.g. agents which protect against UV light (e.g. organic and in-organic UV-absorbers like $TiO_2$ and ZnO, benzophenones, and UV-absorbers which have a synergistic effect on the skin such as e.g. natural or synthetic sunscreen boosters. Other agents may be LIPACIDES (from Seppic), bisabolol and Farnesol.

The oily phase also has a function as a diluent of the skin-friendly first lipid, thus, contributing to a reduction of the production costs of an emulsion according to the invention.

The oily phase comprises a second lipid such as a mono-, di- or triglyceride.

The second lipid of the oily phase is suitably selected from vegetable fats and animal fat and mixtures thereof. The lipid component may also be synthetic oils like e.g. Prisorine 2039 (isostearyl isostearate, CAS No. 41669-30-1), Prisorine 2041 (glyceryl triisostearate, CAS No. 66085-00-5), Estol 3603 (glycerol tricaprylate/caprate, CAS. No. 65381-09-1) and Estasan PR 8-60 (propyleneglycol dicaprylate-dicaprate, CAS No. 977060-55-1).

Examples of suitable vegetable fat are avocado oil, coconut fat, cocoa butter, rapeseed oil, maize oil, sesame oil, olive oil, soybean oil, palm oil, grape seed oil, almond oil, linseed oil, peanut oil, walnut oil, tall oil, thistle seed oil, wheat germ oil, sunflower oil, poppy-seed oil, cottonseed oil, persic oil, apricot oil, jojoba oil, castor oil, hydrogenated vegetable oils, CREMEOL PS 6, PSO, PSW, (Aarhus Olie) and mixtures thereof.

A vegetable lipid derived from plant species from the family Limnanthaceae such as *Limnanthes alba* has especially useful properties in connection with the present invention (cf. the discussion under the heading "Skin-friendly first lipid"; the other lipids mentioned as skin-friendly first lipids may of course also be suitable as second lipids; however, for economical reasons these lipids are normally used in an emulsion according to the invention in combination with at least one of the synthetic oils, vegetable oils and animal fats mentioned above. Meadowfoam seed triglyceride is extracted from Limnanthes alba and is discussed above.

Examples of suitable lipids derived from animals are fish oils, bird fat (such as e.g. Kalaya® oil derived from the emu), domestic animal (pig, cattle, sheep, goats) body fats, wool fat (lanolin), and whale oil, and mixtures thereof.

In a specific embodiment according to the invention an oil comprising a triglyceride of an saturated and relatively short-chain fatty acid ($C_8$–$C_{10}$), namely glycerol tricaprylate/caprate optionally in combination with CREMEOL PS 6 has proved suitable.

The concentration of the second lipid in an emulsion according to the invention is typically in a range corresponding to from about 0.5 to about 60% w/w such as, e.g., from about 1 to about 45% w/w, from about 2 to about 40% w/w, from about 3 to about 35% w/w, from about 5% to about 30% w/w, from about 7 to about 25% w/w or from about 10% to about 20% w/w.

It is believed that a combination of a first and a second lipid in an emulsion according to the invention is advantageous with respect to i) obtaining a suitable oily deposit on the skin (or hair), ii) obtaining a suitable deposit of any agent (cf. above) added to the emulsion with a view of obtaining a beneficial effect on the skin, iii) lowering the production costs of an emulsion according to the invention, and iv) obtaining a suitable cleansing effect including removal of unwanted tensides.

The sum concentration of the first and the second lipid in the emulsion is typically in a range corresponding to from about 1.5 to about 50% w/w such as, e.g., from about 3 to about 45% w/w, from about 5% to about 40% w/w, from about 7% to about 35% w/w, from about 10% to about 30% w/w or from about 15% to about 25% w/w.

Other Important Perspectives

With a view to the environment, an important feature of an emulsion according to the invention is that the emulsion can be degraded into substances which are relatively non-toxic to the environment. Thus, at least a significant part of the individual components in the oily phase and the aqueous phase have suitable ecotoxicological properties so that formation of substances which are hazardous to the environment is substantially minimized when the waste water containing the components are subjected to degradation in a purifying process, and so that the degradation of the individual components in the purifying process is relatively fast. The purifying process may take place in a sewage disposal plant.

Furthermore, and also with a view to the environment, it is very advantageous that the emulsion upon application on the skin and flushing with a liquid (or alternatively, that the emulsion when diluted with an appropriate liquid as discussed above) separates into an oily phase and an aqueous phase. This separation means that the oily phase can be collected in suitable oil separators whereas the aqueous phase can be led out together with waste water.

As mentioned above, an emulsion according to the invention has the ability to separate into at least to separate phases. Thus, an emulsion according to the invention—when diluted with tap water (or another relevant flushing medium) having a degree of hardness of about 8–25 degrees such as about 15–25 degrees such as e.g. 18 degrees in a volume or weight of 100 parts of water to one part of the emulsion at ambient or room temperature—is separated into at least two distinct phases after standing for at the most 24 hours such as e.g. 24 hours, 4 hours, 2 hours, 1 hour or 30 minutes, 5 minutes, 1 minute at ambient or room temperature.

As documented in the Examples herein, an emulsion according to the present invention has a remarkably good storage stability. This finding is very positive and also surprising in that the emulsions tested are water-in-oil emulsions having a content of natural soaps (based on a fatty acid derivative). In general it has been observed that a combination of a natural soap and an oil in an oil-in-water emulsion decreases the storage stability substantially. In this connection it should be mentioned that an emulsion according to the invention should be properly homogenized in order to secure maximum storage stability.

In the experimental section herein a number of non-invasive tests are described. These tests are applicable either alone or, preferably in any combination, for evaluating the effect of treatment of the skin and/or for evaluating which effect an emulsion according to the invention has on skin surfaces upon use. In this connection reference is made to Serup, J., Skin Research and Technology 1995; 1: 109–114, "EEMCO guidance for the assessment of dry skin (xerosis) and ichthyosis: clinical scoring systems", Loden, M., Skin Research and Technology 1995; 1: 101–108, "Biophysical methods of providing objective documentation of the effects of moisturizing creams", Hannuksela, A., and Hannuksela, M., Contact Dermatitis, 1995, 32, 163–166, "Irritant effects of a detergent in wash and chamber tests", and Paye, M., Van der Gaer, D. and Morrison, B. M. Jr, Skin Research and Technology 1995; 1; 123–127, "Corneometry measurements to evaluate skin dryness in the modified soap chamber test".

An important feature of an emulsion according to the invention is its ability to deposit lipid on the skin onto which the emulsion has been applied. Thus, when the skin on the antecubital fossa (flex area of elbow) sebum content was determined by employing a SebumeterG SM 810 (Courage+ Khazaka electronics GmbH, Cologne, Germany) as described in Example 7 herein, the sebumeter value after 40 washings should at least be the same as the starting value (in the Example 7 this value is 2).

In connection with treatment of desiccated skin or otherwise injured skin, a measure of the effect of the treatment may be made by measuring the transepidermal water loss. The treatment normally continues until the transepidermal water loss (TEWL), determined as described in the Examples, has decreased compared with the transepidermal water loss measured immediately before initiation of the treatment or, alternatively, compared with the transepidermal water loss measured after application of a conventional skin cleansing product Furthermore, and also as described in Example 7 herein, the TEWL value should be of the same order of magnitude (i.e. the same value as the starting value ±10% or 15%) after 40 washings as compared with the value before any washing.

Finally, the corneometer value when tested according to Example 7 herein should be of the same order of magnitude (i.e. the same value as the starting value ±10% or 15%) after 40 washings as compared with the value before any washing.

An emulsion according to the invention is typically in the form of a lotion. Preferably, the lotion has a viscosity corresponding to that of liquid soaps. However, there may be situations where an emulsion according to the invention may be presented in the form of a creme or a shampoo.

An emulsion according to the invention has proved to be effective against lice present on humans. Thus, it is believed that the effect observed is mainly due to the presence in the emulsion of a skin-friendly first lipid possible in combination with the other constituents in the oily phase and possible also in combination with the at least one surfactant/emulsifier [the combination of the surfactant/emulsifier/soap is believed to be of importance in connection with the cleansing ability and the ability of emulsifying oily dirt or substances and in connection with the ability of the emulsion to remove unwanted microorganisms or other unwanted organisms (lice etc.)]. An emulsion according to the invention (e.g. PLUM Washing lotion as described in the examples herein)—when applied to human verminous hair and left for 10 min—has proved to be capable of reducing the number of adult lice and their eggs with at least 60% and, furthermore, it is contemplated that application of 100% of a skin-friendly first lipid (as defined herein) will reduce the number with at least 90%.

Especially, emulsions comprising a skin-friendly lipid such as, e.g., a triglyceride comprising at least 90% of long chain $C_{20}$–$C_{22}$ fatty acids have proved to be effective against certain parasites. Accordingly, the invention also relates to the use of an emulsion according to the invention and especially to the use of a skin-friendly lipid such as, e.g., a triglyceride comprising at least 90% of long chain $C_{20}$–$C_{22}$ fatty acids for the treatment or prophylaxis of the presence of parasites such as, e.g., lice, fleas and scabies on mammals such as humans, domestic animals and pets. Especially, the emulsions described in Examples 1 and 2 here in have proved to have therapeutic effect. This effect may be due to only one of the ingredients or to a combination of one or more (e.g. all) of the ingredients, or it may be due to the very advantageous cleansing properties of the emulsion. At present at least Meadowfoam seed oil is believed to have effect against the relevant parasites, but this does riot exclude that the other ingredients also may prove to be active agents against parasites.

More specifically, an emulsion according to the invention or a skin-friendly lipid as defined herein or compositions thereof can be used against parasites belonging to the phylum Arthropoda. Many parasites are host-specific, i.e. a specific species is only found on e.g. a human and not on an animal like a dog or a cat and vice versa. In the following the discussion is directed to human use but it is clear that whenever relevant the statements given also apply for veterinary use for the treatment and/or prophylaxis of veterinary relevant parasites.

Only a few Arthropoda species play a role as parasites on humans. Many more play a significant role as vectors for many infectious diseases. The medically most important arthropods are found in the classes Insecta and Arachnoidea. Relevant orders within the class Insecta are: Siphonaptera (fleas), Phthiraptera (lice), Diptera (mosquitos and flies), Hemiptera (bug), Hymenoptera (bees, wasps, ants), and Orthoptera. In connection with the present invention, especially the use against Siphonaptera, Phthiraptera and Hemiptera is considered as most important.

The order Siphonaptera includes Pulicidae, more specifically the genera Pulex (e.g. *P. irritans*), Ctenocephalides (e.g. *C. canis* and *C. cati*), and Xenopsylla (e.g. *X. cheopsis*).

The order Phtiraptera includes i) Mallophaga including the Trichodectidae family and more specifically the genus Trichodectes (e.g. *T. canis*), and ii) Anoplura including the Pediculidae family and more specifically the genera Pediculus (e.g. *P. humanus* var. capitis and *P. humanus* var. *corporis*) and Phthirus (e.g. *P. pubis*).

The order Hemiptera includes two families, namely Cimicidae and Revuviidae. To the Cimicidae family belongs the genus Cimex (e.g. *C. lectularius, C. hemipterus* and *C. boueti*) and to the Revuviidae family belongs the genera i) Tratoma (e.g. *T. infestans* and *T. sanguisuga*), ii) Rhodnius (e.g. *R. prolixus*) and iii) Panstrongylus (e.g. *P. megistus*).

A relevant order within the class Arachnoidea is Acarida. To the order Acarida belong the following suborders: Ixodina (e.g. lxodidae including the genera Ixodes, Demacentor, Amblyomma, Hyalomma, Haemaphysalis, Rhipicephalus, and Argasinae including the genera Argas, Ornithodoros, and Otobius), Mesostigmatina (e.g. Dermanyssidae including the genera Demanyssus and Ornithonyssus), Trombidiformina (e.g. including the genera Cheyletiella, Trombicula and Demodex), and Sarcoptiformina (e.g. including the families of Sarcoptidae [e,g, Sarcoptes and Notoedres], Psoroptidae [e.g. Psoroptes, Chorioptes and Otodectes], and Acaridae [e.g. Acarus].

An emulsion according to the invention may be used for treating an individual suffering from one or more of the above-mentioned parasites. Most suitable, an emulsion comprises the skin-friendly lipid in a concentration where it is effective against the parasite in question. A suitable concentration is a concentration of at least 5% w/w such as at least 6% w/w, at least 10% w/w, at least 15% w/w, at least 20% w/w, or at least 30% w/w. When Meadowfoam seed oil is used as the skin-friendly lipid the concentration may be in any range from 1–100% w/w as this oil is believed to be an active substance against the parasites mentioned above. Especially, Meadowfoam seed oil has proved to be active against all types of lice (e.g. *Pediculus capitis, Pediculus corporis* and *Pediculosis pubis* or *Phthirus pubis,* and the corresponding species where an animal is the host).

Other Ingredients

An emulsion according to the invention may also comprise various pharmaceutically or cosmetically acceptable excipients or additives such as those which usually are employed in cosmetic or pharmaceutical compositions. Examples are pH adjusting agents such as buffers (such as e.g. citric acid, phosphate buffers, etc.), stabilizing agents (such as e.g. antioxidants like citric acid, sorbic acid, benzoic acid, ascorbic acid, tartaric acid, tocopherols, etc.), chelating agents (such as e.g. EDTA), preservatives (such as, e.g., phenoxyethanol, methylparaben, ethylparaben, propylparaben, butylparaben, sodium butylparaben, and mixtures thereof), flavouring agents, coloring agents, foaming agents, viscosity adjusting agents, thickening agents, spreading agents, pearl gloss agents, agents which protect the skin against aggressive substances in water, atmospheric air and on solid surfaces (examples of such agents include salts, pigments, fats, esters etc.), agents which have an adstringent effect on the skin (e.g. Witch hazel extract, aluminium salts, etc.), agents which accelerate re-epithelialization of the skin or which are anti-irritants or anti-inflammatory substances (such as, e.g., bisabolol, sucralfate, LIPACIDE, gauaiazulene, poly-unsaturated fatty acid derivatives from plant seed oils and other vegetable sources, essential fatty acids and eicosanoids, extracts from Sea Whip Flutec (F 2 Chemicals, France), etc.), liposomes containing active agents like α-hydroxy acids and other actives for the skin, humectants (such as, e.g., lanolin bases liposomal material, ureas, lactates, hydrolyzed proteins, glycerin, diglycerin, polyglycerin, PCA's, sorbitol, collagens, Shellac derivatives, 2-methyl-1,3-propane diol, etc.), protecting agents (such as, e.g. collagen, elastin, chitosan, salts, waxes, long chain alcohols, etc.). Other relevant additives are:

Extracts such as the ones mentioned in combination with the first lipid, and such as, e.g., acacia extract, alfalfa extract, algae extract, aloe extract aloe vera gel, aloe vera gel condensed, althea extract, anise extract, apple extract, apricot extract, apricot kernel oil, arnica extract (*arnica montana* L), artichoke extract, asafoetida extract, avocado extract, azulene, balm mint extract, balm mint oil, banana extract, barley extract, bee pollen extract, bioflavonoids, birch leaf extract (*betulla pendula rotl*-L), black cohosh, black currant extract, black walnut extract, bladderwrack extract (*fucus vesiculosos* L), borage extract, botanical extracts, burdock extract (*arctium lappa* L), burnet extract, butcher's broom extract (*ruscus aculeatus* L), calendula extract, camomile extract (*matricaria charmomila* L), caper extract, carrageenan extract, carrot extract (*daucus carota* L. var. *sativa*), carrot oil, centella (*centalla asiatica urban*), cherry bark extract, cinchona extract, cinquefoil extract, citroflavonoid water soluble, citrus bioflavonoid complex, clover blossom extract, coltsfoot extract, cornfrey extract, coneflower extract, cornflower extract (*echinacea angustifolia monch*), corn silk extract, couch grass (*agropyron repens beauv.*), crataegus extract (*crataegus oxycantha* L), cucumber extract, cypress extract, dandelion extract (*taraxacum officinalis weber*), elder flower extract, eleuterococcus, elm bark extract, ethyl alcohol (and) licorice extract, eucalyptus extract, everlasting extract, fennel extract, fenugreek extract (*trigonella foenum-graecum* L), fern extract, gardenia extract, garlic extract, gerrtian extract, gingko biloba extract, ginko extract, ginseng extract (*panax ginseng* C. A. Meyer), glycyrrhetinic acid, glycyrrhizic acid, grape extract, grape leaf extract, grape skin extract, guarana extract, Hawaiian ginger extract, hayflower extract, helichrysum (*helichrysum italicum* G. Don), henna extract (*lawsonia inermis*), hesperidin complexes, hesperidin methyl chalcone, hibiscus extract, hops extract (*humulus lupulus* L), horse chestnut extract (*aesculus hippocastanum* L), horsetail extract (*equisetum arvenese* L), hypericum extract, indian cress extract, ivy extract (*hedera helix* L), juniper extract (*juniperus communis* L), kelp extract, kiwi extract, laminaria extract, lavender extract, lemon balm (*melissa officinalis* L), lemon extract, lettuce extract, licorice extract, linden extract (*tilla argentea desf.*), madder (*rubia tinctorum* L), mallow extract (*malva silvestris* L), matricaria extract English, milfoil extract (*achillea millefolium* L), mistletoe extract, mushroom extract, myrrh extract (commphora myrra (Nees), nettle extract (*urtica diocia* L), oak root extract, oat extract, onion extract orange blossom extract, orange flowers extract, pansy extract, parsley extract, pellitory extract, pennyroyal extract, peppermint extract (*mentha piperita* L), periwinkle extract, pine needle extract, plantain extract (*plantago lanceolata*), pollen extract, quince seed, rauwolfia extract, restharrow extract, rhatany extract (*krameric triandra ruix* et pav.), rhubarb root extract, rice bran extract, rose hips extract, rosemary extract (*rosmarinus officinalis*), sage extract (*Salvia officinalis* L), sambucus extract, sanguinaria root extract, saponaria extract, sea weed extract, soy extract, soy protein, soy sterol, spearmint extract, sulfur tar complex, sunflower extract, sweet clover extract, tea extract, tea tree oil, thistle extract, thyme extract (*thymus vulgaris*), tomato extract, tormentill extract, valerian extract, walnut extract (*junglas regia* L), water cress extract, wheat bran extract, wheat germ extract, white nettle extract, white willow bark extract, wild indigo, witch hazel extract (*hamamelis virginia* L), yarrow extract, and zedoary oil (and) ginger oil (and) cinnamon oil;

humectants like acetamide MEA, acetamido propyl trimonium chloride, calcium stearoyl lactylate, chitosan PCA, diglycerol lactate, ethyl ester of hydrolyzed silk, fatty quaternary amine chloride complex, glycereth-7, glycereth-12, glycereth-26, glycereth-4.5 lactate, glycerin, diglycerin, polyglycerin, honey, hydrolyzed fibronectin, lactamide MEA, lactamide N-(2-hydroxyetheryl), mannitol, methyl gluceth-10, methyl gluceth-20, methylsilanol PCA, panthenol, PCA, PEG-4, PEG-8, polyamino sugar condensate, quaternium-22, sea salts, sodium capryllactylate, sodium hyaluronate, sodium isostearoyl lactylate, sodium lactate, sodiumlauroyl lactylate, sodium PCA, sodium polyglutamate, sodium stearoyl lactylate, soluble collagen, sorbitan laurate, sorbitan oleate, sorbitan sesquiisostearate, sorbitan stearate, sorbitol, sphingolipids, TEA-PCA;

moisturizers such as, e.g., aloe vera gel, aloe vera gel condensed, aloe vera gel freeze-dried powder, aloe vera gel oil extract, amino acid, amniotic fluid, avocadin, calcium protein complex, cashew oil, chia oil, chitin, chitosan, chitosan PCA, cholesteric esters, chondroitin sulfate, collagen, collagen amino aids, copper protein complex, dioctyl maleate, dipentaerythritol fatty acid ester, elastin, ethyl panthenol, evening primrose oil, glycereth-12, glycosphingo lipids, honey, hyaluronic acid, hybrid safflower oil, hydrogenated polyisobutene, hydrolyzed collagen, hydrolyzed elastin, hydrolyzed fibronectin, hydrolyzed mucopolysaccharides, hydrolyzed silk, hydrolyzed wheat protein, jojoba esters, keratin amino acids, kiwi fruit extract, lactamide MEA, lanolin alcohol, liposomes, live yeast cell derivative liposome, marina polyaminosaccharide, mineral oil, mink oil ethyl ether, mucopolysaccharides, mucopolysaccharides, palmetto extract, pantethine, paraffin, PEG-4, PEG-6,- PEG-8, PEG-12, PEG-100 stearate, perfluoropolymethyl-isopropyl ether, petrolatum, petroleum wax, pistachio oil, placenta extract, plankton extract, polyamino sugar condensate, polybutene, polyglyceryl methacrylate, polypentaerythrityl tetralaurate, PPG-10 butanediol, PPG-20 methyl glucose ether distearate, royal jelly extract, saccharide isomerate, selenium protein complex, serum albumin, sodium hyaluronate dimethylsilanol, sodium lactate methylsilonol, sodium mannuronate methylsilanol, soluble collagen, super oxide dismutase, super oxide dismutase liposome, tissue extract, tocopheryl linoleate;

other skin protectants such as, e.g., allantoin, aloe vera gel, anise extract, avocado oil unsaponifiables, carboxymethyl chitin, chondroitin sulfate, collagen, collagen amino acids, embryo extract, glyceryl ricinoleate, hydrolyzed animal elastin, hydrolyzed milk protein, hydrolyzed vegetable protein, linoleic acid (and) linolenic acid (and) arachidonic acid, liposomes, perfluoropolymethyl-isopropyl ether, plankton extract, and spine marrow extract.

An emulsion of the invention may further comprise active agents such as disinfectants or antiseptics, drug substances including vitamins. Incorporation of one or more disinfectants or antiseptics is especially useful in those situations where it is important to inactivate the microorganisms which remain on the skin after normal cleansing. Incorporation of a drug substance is of special interest in connection with application of drug substances to the skin for the prevention or treatment of various skin disorders or in connection with drug substances which advantageously are administered topically for percutaneous absorption. The disinfectant and/or drug substance should preferably have a solubility in the oily phase which secures that the substance is delivered to the skin in an effective amount.

In those cases where a disinfectant or antiseptic and/or a drug substance is present in an emulsion according to the invention, the constitution of the oily phase of the emulsion may be determined using solubility parameters to predict the solubility of the disinfectant/antiseptic/drug substance in the oily phase. Application of solubility parameters is described e.g. in Shell Chemical: Technical Bulletin ICS(x)/75/1, in Hansen, C. M.: "The absorption of liquids into the skin" UDK No. 66.062 published by Scandinavian Paint and Printing Ink Research Institute, and in Barton, A. F. M.: "CRC Handbook of Solubility Parameters and Other Cohesion Parameters", CRC Press Inc., Florida.

Examples of suitable disinfectants and antiseptics are ambazone, bithionol, bromsalans, dibromsalan, metabromsalan, tribromsalan, cethexonium bromide, chlorhexidine acetate, chlorhexidine gluconate solution, chloroazodin, chlorocresol, chlorothymol, chloroxylenol, clorophene, cresol, dichlordimethylhydantoin, dichlorobenzyl alcohol, dichloroxylenol, dofamium chloride, domiphen bromide, ethacridine lactate, methylbenzethonium chloride, nitromersol, noxythiolin, and triclosan. Other relevant examples are sodium pyrithione, sodium ricinoleate, thimerosal, trichlocarban, undecylenamidopropyltrimethyl ammonium methosulfate, undecylenic acid, zinc pyrithione, and zinc undecylenate.

The expression "drug substance" as used herein broadly includes any compound, or mixture thereof, that is able to produce a beneficial effect on the human to whom the drug substance has been given. Thus, drug substances include any physiologically or pharmacologically substance that produces a localized or systemic effect in mammals including humans. Examples of drug substances are found in many therapeutic groups including antiinflammatory drugs, analgesics, tranquilizers, cardiac glycosides, narcotic antagonists, antiparkinsonism agents, antidepressants, antineoplastic agents and immunosuppressants, antiviral agents, antibiotic agents, appetite suppressants, antiemitics, antihistamines, antimigraine agents, coronary, cerebral or peripheral vasodilators, antianginals, calcium channel blockers, hormonal agents, contraceptive agents, antithrombotic agents, antihypertensive agents, chemical dependency drugs, local anaesthetics, corticosteroids, dermatological agents, and the like, vitamins like vitamin A such as all-trans retinol, retinol acetate, retinol palmitate, retinol propionate, betacarotene, halibut-liver oil, shark-liver oil, vitamin $B_1$ such as e.g. thiamine hydrochloride, benfotiamine, bisbentiamine, bisbutiamine, bisibutiamine, betoiamine hydrochloride, cetotiamine hydrochloride, cocarboxylase, cycotiamine, fursultiamine, vitamin $B_2$ such as e.g. riboflavine, riboflavine tetrabutyrate, flavine adenine dinucleotide, vitamin $B_6$, vitamin $B_{12}$ such as e.g. cobalamins, $B_{12}$TAM, cobamamide, cyanocobalamin, mecobalamin, other vitamins of the B group, vitamin C such as e.g. ascorbic acid, vitamin D such as e.g. ergocalciferol (vitamin $D_2$), cholecalciferol (D3), 25-hydroxy-cholecalciferol or calcifediol, 1,25dihydroxycholecalciferol or calcitriol, 1α-hydroxycholecalciferol or alfacalcitriol, dihydrotachysterol, alfacalcidol, calcifediol, calcitriol, cholecalciferol, cod-liver oil, dihydrotachysterol, ergocalciferol, vitamin E, alpha tocopherols, tocopheryl nicotinate, tocopherylquinone, wheat-germ oil, vitamin K such as e.g. phytomenadione, menadiol sodium diphosphate, menadione, vitamin P.

A very interesting group of drug substances are sucrose sulfate esters such as sucralfate, sucrose octasulfate and salts, esters and complexes thereof. Most suitably the sucrose sulfate esters or derivatives thereof are soluble in the oily phase of an emulsion according to the invention.

Other interesting substances which may be incorporated in an emulsion according to the invention are sunscreens and/or WV-absorbers, insect repellants, and/or anti-parasitic agents against parasites like lice, fleas, scabies, bugs, and mites.

Examples of relevant sunscreens are allantoin, PABA, p-aminobenzoates, benzophenone-2, benzophenone-6, benzoresorcinol, benzyl salicylate, cinoxate, dioxybenzone, esculoside, ethyl 4-bis(hydroxypropyl)aminobenzoate, ethylhexyl p-methoxycinnamate, etocrylen, glyceryl aminobenzoate, homosalate, methyl salicylate, methyl anthranilate, methyl eugenol, 3-(4-methylbenzylidene) boran-2-one, mexenoe, octabenxone, octocrylene, oxybenzone, padimate, 2-phenyl-1H-benzimidazole-5-sulphonic acid, and sulisobenzone. Other relevant sunscreens or UV-absorbers are: sunscreens like 3-benzylidene camphor, coffee extract, ethyl salicylate, glyceryl PABA, homosalate, isopropylbenzylsalicylate, menthyl anthranilate, nylon-12 (and) titanium dioxide, octyl dimethyl PABA, octyl methoxycinnamate, octyl salicylate, octyl triazone, orizanol, PEG-25 PABA, TEA-salicylate, titanium dioxide, zinc oxide; UV-A absorbers like benzophenone-1, benzophenone-3, benzophenone-4, bensophenone-8, benzophenone-9, benzophenone-11, benzophenone-12, butyl methoxydibenzoylmethane, 4-isopropyl dibenzoyl methane, and avocadin; and UV-B absorbers like argana oil, DEA-methoxycinnamate, drometrizole, ethyl dihydroxypropyl p-aminobenzoic acid, etocrylene, isopropyl methoxycinnamate, 3-(4-methylbenzylidene)-camphor, octocrylene, octrizole, octyl dimethyl PABA, octyl methoxycinnamate, octyl salicylate, octyl triazone, PABA, shea butter ethoxylated, TEA-salicylate, tri-PABA-panthenol.

Examples of relevant insect repellents are butopyronoxyl, butylethylpropanediol, dibutyl phthalate, diethyltoluamide, dimethyl phthalate, and ethohexadiol. The concentration of the active drug substance—when present—in the emulsion depends on the active substance in question, its potency, the severity of the disease to be prevented or treated, the age and condition of the patient. Methods applicable to selecting relevant concentrations of active substance in the emulsion are well known for a person skilled in the art and may be performed according to established guidelines for good clinical practice (GCP) or Investigational New Drug Exemption ("IND") regulations as described in e.g. Drug Applications, Nordic Guidelines, NLN Publication No. 12, Nordic Council on Medicines, Uppsala 1983 and Clinical Trials of Drugs, Nordic Guidelines, NLN Publication No. 11, Nordic Council on Medicines, Uppsala 1983. A person skilled in the art would by use of methods described in standard textbooks, guidelines and regulations as described above as well as common general knowledge within the field be able to select the exact dosage regimen to be implemented for any selected active substance and dosage form using merely routine experimentation procedures.

In a further aspect, the invention relates to a method for the preparation of an emulsion. An emulsion according to the invention may be prepared using procedures which are well known for a person skilled in the art. In the experimental section examples of a preparation of an emulsion according to the invention are given.

In a further, aspect the invention relates to an oil-in-water emulsion comprising an oily phase at least part of which consists of a triglyceride having at least 90% of long chain $C_{20}$–$C_{22}$ fatty acids (see above for a detailed discussion). The emulsion is capable of separating into at least two distinct phases after standing for 24 hours when diluted with tap water in a volume of 100 parts of water to one part of the emulsion at ambient temperature. The triglyceride typically comprises a combination of a monoenoic and a dienoic fatty acid component, the ratio of the monoenoic fatty acid component to the dienonic fatty acid component being in a range corresponding to from about 1:99 to about 99:1 and the two unsaturated bonds of the dienoic fatty acid component being spaced from each other by at least 5 carbon atoms.

In other aspects, the invention relates to a method for cleansing or conditioning a skin surface, comprising applying, to the skin surface, an emulsion comprising a skin-friendly oily phase and an aqueous phase, the emulsion being stabilized by containing at least one surfactant/emulsifier, and flushing the skin surface with a liquid, whereby the at least one surfactant/emulsifier is substantially removed from the skin surface onto which the emulsion has been applied and thereby leaving at least a part of the oily phase on the skin.

In a still further aspect, the invention relates to a method for treating human skin comprising applying, to the skin surface, an emulsion comprising a skin-friendly oily phase and an aqueous phase, the emulsion being stabilized by containing at least one surfactant/emulsifier, the at least one surfactant/emulsifier being capable of being substantially removed from a skin surface onto which the emulsion has been applied and from the emulsion by flushing with a liquid, thereby leaving at least a part of the oily phase on the skin, until the transepidermal water loss (TEWL), determined as described in the Examples, has decreased compared with the transepidermal water loss measured immediately before initiation of the treatment.

In still further aspects, the invention relates to i) Meadowfoam seed oil as a therapeutic agent, ii) use of Meadowfoam seed oil for the manufacture of a pharmaceutical composition for the treatment and/or prevention of mammalian parasites belonging to the phylum Arthropoda, iii) use of an oil-in-water emulsion for the treatment and/or prevention of mammalian parasites belonging to the phylum Artliropoda, iv) a method for treating mammals against parasites belonging to the phylum Arthropoda, the method comprising administering to the mammal suffering therefrom an effective amount of Meadowfoam seed oil, v) a method for treating mammals against parasites belonging to the phylum Arthropoda, the method comprising administering to an individual suffering therefrom an effective amount of an oil-in-water emulsion, vi) use of Meadowfoam seed oil as a sun screen, vii) use of a combination of Meadowfoam seed oil and shea butter for the manufacture of a pharmaceutical composition for the treatment or prevention of mammalian parasites of the phylum Arthropoda, vii) a method for protecting human skin against the sun, the method comprising applying to the human skin an effective amount of Meadowfoam seed oil alone or in combination with a vegetable extract, especially Karite extract, and viii) a method for protection of human skin against the sun, the method comprising applying to the human skin an effective amount of an oil-in-water emulsion.

As will be understood, details and particulars concerning the above-mentioned further aspects of the invention will be the same as or analogous to the details and particulars concerning the emulsion aspect discussed above, and this means that wherever appropriate, the statements above concerning the oil-in-water emulsion also apply to the other aspects of the invention.

Materials and Methods

In the following examples, the following materials are used (listed with the INCI name and the CAS-No.):

| INCI name | CAS-No. available from |
|---|---|
| Aqua | 7732-18-5 |
| Glycerol tricaprylate/caprate | 65381-09-1 |
| | Unichema 3605 |
| Glycerol ricinoleate | 1323-38-2 |
| Grape seed oil | 8024-22-4 |
| | J. Lorenzen, Denmark |
| Meadowfoam triglyceride | 153065-40-8 |
| | The Fanning corporation |
| Cocamide MEA | 68140-00-1 |
| | J. Lorenzen, Denmark |

-continued

| INCI name | CAS-No. available from |
|---|---|
| Cocamidopropyl betaine | 61789-40-0 |
| | Goldschmidt |
| Sulfated castor oil | 8002-33-3 |
| | Henkel |
| C9-11 Pareth 6 | 68439-46-3 |
| | BASF |
| Citric acid | 77-92-9 |
| | NDH, Denmark |
| Tetrasodium EDTA | 64-02-8 |
| | Dan-Chem, Denmark |
| Phenoxyethanol | 122-99-6 |
| Methylparaben | 99-76-3 |
| Propylparaben | 94-13-3 |
| Ethylparaben | 12047-8 |
| Butylparaben | 94-26-8 |
| Sodium butylparabene | |
| Monoethanolamine | |
| Palm kernel fatty acid | |
| Rilanit GROM | |
| Nipabutyl sodium | |
| NaHMF | |

The materials used were all of pharmaceutical, food or cosmetic grade.

The following methods are employed in the experimental section

Determination of Acid Value

The acid value gives the amount (in mg) of potassium hydroxide required to neutralize the free acids in 1 g of sample material.

In the present context, the acid value test may suitably be performed in order to i) determine the acid value of an oil-in-water emulsion according to the invention;

ii) determine the acid value of the liquid which is used as a flushing medium. In those cases where the content of free fatty acid in the oil-in-water emulsion is low or absent and where it is anticipated that the breaking of the emulsion by a flushing medium is insufficient, a compensation can be made by securing that the flushing medium (such as, e.g., water) has a suitable acid value (e.g. by adding free fatty acid or other acids to the flushing medium and, alternatively, also adding salts (e.g. $Ca^{2+}$ or $Mg^{2+}$ salts), conditioning agents and/or flocculating agents). During the cleansing/washing process 0.25–1% of the emulsion is normally used in relation to the flushing medium. If the washing product does not contain any excess of free fatty acid then it can be calculated that the flushing medium should have an acid value in the range of x/100-x/400, where x is the acid value normally aimed at for the cleansing/washing product itself in those cases where free fatty acid is present. Thus, if x=36, then the acid value of the flushing medium should be in a range corresponding to from about 0.1 to about 0.6;

iii) determine the content of free fatty acids in the liquid used, after flushing the skin with a liquid upon application to the skin of an emulsion according to the invention. When the skin unto which an emulsion according to the invention has been applied is flushed with a suitable liquid, the emulsion separates into at least two distinct phases, i.e. an aqueous phase and an oily phase. Thus, the stabilizing effect of the surfactant/ emulsifier is reduced or even eliminated most likely due to a degradation of the surfactant/emulsifier. The liquid is collected after flushing and the acid value is determined in the aqueous phase as well as in the oily phase in order to determine the content of fatty acids in the at least two distinct phases.

The acid value is determined by use of a Mettler DL 25 titrator (Mettler, Denmark).

Before measurement of a sample, the titrator is calibrated using at least 40 ml of each of two buffers having a pH of about 7.00 and 4.01, respectively. The calibration is performed in accordance with the instructions given by the manufacturer. The acid value of a sample is then measured by adding 40.0 ml of neutralized isopropyl alcohol to the amount of sample required for running the test (0.4–0.6 g).

An emulsion according to the invention should preferably have an acid value of about 10–60 mg KOH/g, such as, e.g., about 20–55 mg KOH/g, about 30–45 mg KOH/g, about 35–40 mg KOH/g or about 36.0–37.0 mg KOH/g.

Determination of pH

The pH of an emulsion according to the invention is determined by employing a Mettler Delta 350 apparatus (Mettler, Denmark). Before measurement of the pH of a sample, the apparatus is calibrated using three buffers having a pH of 7.00, 4.01 and 10.01, respectively. The measuring electrode A is a Mettler electrode Lot. 406-M6-DXX-57/25 and as reference electrode B a Mettler electrode Lot. U402-88TE-57/120 is used. A temperature sensor is placed in the buffer receiving the measuring electrode, and the buffer receiving the reference electrode is stirred during calibration.

When the apparatus is calibrated, pH of a sample is measured in the following manner.

A 50% pH value is determined by using 12 g of tap water mixed with 12 g of sample. The resulting mixture is cooled to about 17–18° C as the temperature increases during measurement. The mixture is stirred. During measurement, stirring is performed at the reference electrode and the pH is measured according to the instructions given by the manufacturer.

A 100% pH value is determined by using a sample of an emulsion according to the invention and by cooling the sample to about 20° C. Stirring is performed at the reference electrode and the pH measurement is performed in accordance with the instructions given by the manufacturer.

Determination of Viscosity

The viscosity is determined by means of a Brookfield DV 3 HA apparatus employing a plate cone CP52, CP40 system as a spindle. The temperature is kept constant during measurements (19.9–20.1° C.). Each sample is subjected to 10 individual measurements and the result given is the average thereof. In the table given below, the results of measurements of an emulsion according to the invention are given.

| | | Model: HA | Spindle: CP52 | | | | |
|---|---|---|---|---|---|---|---|
| | File: LJ_27 | | Sample: Plum Cleansing lotion | | | | |
| Item # | Speed RPM | Torque % | Viscosity cP | SH Stress D/cm$^2$ | SH Rate 1/s | Temp ° C. | Time MM:SS |
| 1 | 10.0 | 14.9 | 2929 | 585.9 | 20.0 | 20.0 | 00:20 |
| 2 | 10.0 | 15.0 | 2949 | 589.8 | 20.0 | 19.9 | 00:20 |
| 3 | 10.0 | 15.1 | 2969 | 593.7 | 20.0 | 19.9 | 00:20 |
| 4 | 10.0 | 15.2 | 2988 | 597.7 | 20.0 | 19.9 | 00:20 |
| 5 | 10.0 | 15.3 | 3008 | 601.6 | 20.0 | 20.0 | 00:20 |
| 6 | 10.0 | 15.3 | 3008 | 601.6 | 20.0 | 20.0 | 00:20 |
| 7 | 10.0 | 15.4 | 3028 | 605.5 | 20.0 | 19.9 | 00:20 |
| 8 | 10.0 | 15.4 | 3028 | 605.5 | 20.0 | 19.9 | 00:20 |
| 9 | 10.0 | 15.4 | 3028 | 605.5 | 20.0 | 19.9 | 00:20 |
| 10 | 10.0 | 15.4 | 3028 | 605.5 | 20.0 | 19.9 | 00:20 |

Determination of Transepidermal Water Loss (TEWL)

Transepidermal water loss (TEWL) is a sensitive indicator of the integrity of *stratum corneum* and can therefore be used as a measure of skin barrier damages.

TEWL and evaporation of water from the surfaces are measured with a Tewameter TM 20 (Courage+Khazaka electronic GmbH, Cologne, Germany). Important factors to consider during the measurements are air convection, room temperature and ambient humidity. The guidelines followed for the measurement of TEWL have been published by the standardization group of the European Contact Dermatitis Society (Pippagoda, J., Tupker, R. A., Agner, T. and Serup, J. *Guidelines for transeuidermal water loss (TEWL) measurement. A report from the tandardization group of the European Contact Dermatitis Society.* Contact Dermatitis 1990, 22 164–178). The measurements were performed in accordance with the instructions given by the manufacturer.

Determination of Skin Elasticity

Mechanical testing of skin is normally considered difficult, since the skin is a stratified composite material and the relationship between the various layers is complex.

Parameters used to describe skin mechanics are elasticity (see below), hysteresis (reflecting the creeping phenomenon) and distensibility (the maximum distension achieved).

Human skin is visco-elastic, i.e. it contains elastic as well as plastic components. Elasticity is the ability of the skin to return to its original position after being stretched. A fully elastic skin surface will return to its original shape upon mechanical influence, whereas a fully plastic skin does not return to its original shape upon mechanical influence. Young skin, which is fresh and well-supplied with blood, is very elastic. Aged skin, which is less supplied with blood, is more plastic. Furthermore, various parts of the body have different degrees of elasticity and plasticity and different parts of the skin (i.e. skin on the cheek and the forehead) have different elasticity amplitudes.

The elasticity of the skin is measured by employing a Cutometer® SEM 575 apparatus (Courage+Khazaka electronic GmbH, Cologne, Germany). The measurements are performed in accordance with the instructions given by the manufacturer.

Determination of Skin Hydration by Means of Measurement of the Electrical Capacitance As described in the description, the skin can be divided into two layers which seen from the skin surface are: the epidermis and the dermis. *Stratum corneum* is the outermost layer of the epidermis. *Stratum corneum* is of great importance for the moisture regulation of the skin. *Stratum corneum* contains keratin, and what was once living epithelial cells have become horny scales that adhere tightly to one another, except at the surface where they desquamate.

Another important layer within the epidermis is the *stratum lucidum* layer which is present on e.g. human skin covering the body, except the palms of the hands and the soles of the feet. The *stratum lucidum* has special mechanical and chemical barrier functions. It forms a boundary layer between the *stratum corneum* and the living cells of *stratum granulosum* (another layer within the epidermis). *Stratum lucidum* also reacts to changes in humidity/moisture.

Skin moisture influences the formation of a water-sebum film. Such a film forms the basis for the protective functions of the skin. Furthermore, only a moist skin has the desired optimal elasticity and prevents possible ageing signs. The so-called "aged skin" is relatively thin and usually dry and rough in texture. It also tends to wrinkle. Soaps, detergents, surfactants, emulsifiers, etc. are some of the causes of dry skin.

A measure for skin moisture can be obtained by employing a Corneometer® CM 820 (Courage+Khazaka electronic GmbH, Cologne, Germany). The method is based on the fact that the dielectricity constants of water and other substances are different. The tests were performed in accordance with the instructions given by the manufacturer.

Determination of Skin Sebum Content

Skin surface lipids from sebaceous glands and topically applied products are quantified using an opaque lipid-sensitive plastic Mim. When attached to the skin, the film becomes transparent due to the content of lipids and the light transmission through the film is a measure of the amount of lipids per surface area units.

The skin sebum content was determined by employing a Sebumeter® SM 810 (Courage+Khazaka electronics GmbH, Cologne, Germany). The tests were performed in accordance with the instructions given by the manufacturer.

Determination of Skin pH

Skin pH is a measure of the actual skin condition and skin quality. The average pH value of human skin is about 5.5 for women and about 5 for men. The pH value depends on the tested skin area and various exogenic factors. A pH value about 5–5.5 means that the pH of the skin is in the acidic range influencing the bactericidal and fungicidal effect of the skin.

Permanent treatment of the skin with e.g. soaps, cosmetics and pharmaceutical products or chemicals may lead to desiccation of the skin indicated by damages and premature ageing. Normally, soap solutions have pH values above 7. A healthy skin which is exposed to such a soap solution will normally first regain its original pH value about 30 minutes after exposure. A sensitive skin may adjust to a higher pH over a longer period of time which considerably influences its protection functions. Furthermore, cosmetics which remain on the skin cause stress to skin, such as skin having an undesirably high pH value and, thus, the protective function of the skin becomes reduced. pH on the skin can be measured in vivo by use on a non-invasive method employing e.g. a Skin-pH-meter® PH900 (Courage+Khazaka electronic GmbH, Cologne, Germany). The tests were performed in accordance with the instructions given by the manufacturer.

Assessment of Dry Skin (Xerosis) and Ichthyosis

The assessment of dry skin is performed in accordance with the Guidelines published by The European Group on Efficacy Measurement of Cosmetics and other Topical Products (EEMCO) (J. Serup: *Skin Research and Technology* 1995, 109–114).

EXAMPLES

Example 1

Preparation of an Oil-in-water Emulsion According to the Invention

A general method for the preparation of an emulsion according to the invention is first to prepare the aqueous phase by mixing all the water-soluble ingredients except the surfactant/emulsifier, e.g. in the form of a fatty acid, with purified water at 20° C. until the ingredients are dissolved. The fatty acid is then added under a stirring process at ambient temperature to form a soap. After a reaction time of about 1 hour, the remaining ingredients are added one at a time and stirred thoroughly.

More specifically, an oil-in-water emulsion according to the invention and having the composition mentioned below is prepared as described in the following.

Composition of the oil-in-water emulsion:

| Ingredients | % w/w |
| --- | --- |
| I: | |
| Aqua (purified) | 57.94 |
| Tetrasodium EDTA | 0.31 |
| Citric acid | 0.50 |
| MEA 99% | 2.40 |
| Potassium hydroxide 46% | 0.16 |
| II: | |
| Palmitic fatty acid | 11.38 |
| III: | |
| Glycerol tricaprylate/caprate | 13.82 |
| Turkish red oil (sulfated castor oil) | 2.24 |
| Parabene premix (mixture of 70% w/w phenoxyethanol, 20% w/w methylparaben and 10% w/w propylparaben) | 0.73 |
| Tegobetain F50 (cocoamidopropyl betaine) | 5.36 |
| Meadowfoam seed triglyceride | 4.47 |
| Lutensol TO3 (C9-11 Pareth) 6 | 0.69 |

The ingredients mentioned under I are mixed at 20° C. II is added under a stirring process to form a soap. After a reaction time of one hour, the ingredients mentioned under III are added one at a time and stirred thoroughly. pH of the resulting emulsion is 7.5–7.7 measured as described above under the heading "Determination of pH".

Example 2

Composition of Lotions According to the Invention

The ingredients in lotions according to the invention are given in the following table. The preparation of the lotions was performed as described in Example 1.

JL-30 was prepared by mixing the ingredients in the series given. The palm kernel fatty acid had a temperature of 50° C. Rilanit GMRO had a temperature of 37° C. The mixing process was performed at room temperature and the mixture was stirred at an increasing speed of rotation followed by a homogenizing process. Stirring times are given against an increase in minutes counted from the beginning of the process.

In the table, stability data are also given. Four series of stability tests were performed for samples in sealed containers stored at a temperature of −5° C., 20° C., 37° C. and 50° C., res The stability was evaluated by visual inspection and a score of 0, 1 or 2 was given to each sample after inspection. 0 refers to lotions which have separated into two distinct phases, 1 refers to lotions where no tendency of separation is observed, and 2 refers to lotions with tendency to separate into two phases. The initial results show that lotions according to the invention have a good physical stability with regard to the stability of the emulsion formed.

|  | JL-20 w/w | JL-20-1 w/w | JL-21 w/w |
|---|---|---|---|
| Ingredients |  |  |  |
| Water, cold, purified | 60.54% | 60.32% | 57.81% |
| EDTA 40%[a] | 0.32% | 0.32% | 0.30% |
| Citric acid[b] | 0.52% | 0.52% | 0.48% |
| MEA 99%[c] | 2.31% | 2.30% | 2.59% |
| KOH 46% | 0.16% | 0.16% | 0.19% |
| Palm seed fatty acid[d] | 0.00% | 0.00% | 0.00% |
| Coco fatty acid[e] | 11.72% | 11.67% | 12.24% |
| Grape seed oil[f] | 14.54% | 14.45% | 13.82% |
| Turkish red oil[g] | 2.26% | 2.25% | 2.16% |
| Parabene premix[h] | 0.74% | 0.66% | 0.69% |
| Tegobetain F50[i] | 1.86% | 1.84% | 5.27% |
| Meadowfoam seed oil[j] | 4.81% | 4.84% | 4.45% |
| Lutensol TO3[k] | 0.21% | 0.67% | 0.00% |
| SUM: | 100.00% | 100.00% | 100.00% |
| pH: | 6.990 | 7.590 | 7.783 |
| Acid value |  | 35.85 | 37.41 |
| Viscosity[l] | 1500 cp |  | 4800 cp |
| pH[m]/acid value | 6.944 |  | 7.783 |
| Stability Test |  |  |  |
| Acid value | 36.6 | 37.41 |  |
| Day 1 |  |  |  |
| −5° C./20° C. | 1/1 | 1/1 |  |
| 37° C./50° C. | 1/1 | 1/1 |  |
| Day 7 |  |  |  |
| −5° C./20° C. | 1/1 | 1/1 |  |
| 37° C./50° C. | 1/2 | 1/1 |  |
| Day 30 |  |  |  |
| −5° C./20° C. | 1/2 | 1/1 |  |
| 37° C./50° C. | 0/0 | 1/1 |  |
| Day 60 |  |  |  |
| −5° C./20° C. | 1/0 |  |  |
| 37° C./50° C. | 0/1 |  |  |
| Day 180 |  |  |  |
| −5° C./20° C. |  |  |  |
| 37° C./50° C. |  |  |  |

|  | JL-22 w/w | JL-23 w/w | JL-24 w/w |
|---|---|---|---|
| Ingredients |  |  |  |
| Water, cold, purified | 58.94% | 56.42% | 52.20% |
| EDTA 40%[a] | 0.31% | 0.30% | 0.37% |
| Citric acid[b] | 1.05% | 0.63% | 0.56% |
| MEA 99%[c] | 2.23% | 2.01% | 2.49% |
| KOH 46% | 0.17% | 0.15% | 0.17% |
| Palm seed fatty acid[d] | 0.00% | 0.00% | 0.00% |
| Coco fatty acid[e] | 11.54% | 11.13% | 14.02% |
| Grape seed oil[f] | 14.40% | 13.74% | 15.50% |
| Turkish red oil[g] | 0.00% | 2.15% | 2.47% |
| Parabene premix[h] | 0.72% | 0.66% | 0.81% |
| Tegobetain F50[i] | 5.74% | 7.79% | 6.11% |
| Meadowfoam seed oil[j] | 4.53% | 4.35% | 5.02% |
| Lutensol TO3[k] | 0.37% | 0.68% | 0.00% |
| SUM: | 100.00% | 100.00% | 100.00% |
| pH: | 7.091 | 7.249 | 7.261 |
| Acid value | 40.28 | 40.72 | 45.48 |
| Viscosity[l] | 620 cp | 2020 cp | 187900 cp |
| pH[m]/acid value | 7.091 | 7.249 | 7.261 |
| Stability Test |  |  |  |
| Acid value | 40.28 | 40.72 | 45.48 |
| Day 1 |  |  |  |
| −5° C./20° C. | 1/1 | 1/1 | 1/1 |
| 37° C./50° C. | 1/1 | 1/1 | 1/1 |
| Day 7 |  |  |  |
| −5° C./20° C. | 1/1 | 1/1 | 1/1 |
| 37° C./50° C. | 1/1 | 1/1 | 1/1 |
| Day 30 |  |  |  |
| −5° C./20° C. | 1/1 | 1/1 | 1/1 |
| 37° C./50° C. | 1/1 | 1/1 | 0/2 |
| Day 60 |  |  |  |
| −5° C./20° C. |  |  |  |
| 37° C./50° C. |  |  |  |
| Day 180 |  |  |  |
| −5° C./20° C. |  |  |  |
| 37° C./50° C. |  |  |  |

|  | JL-25 w/w | JL-26 w/w | JL-27 w/w |
|---|---|---|---|
| Ingredients |  |  |  |
| Water, cold, purified | 59.20% | 57.94% | 58.00% |
| EDTA 40%[a] | 0.30% | 0.31% | 0.30% |
| Citric acid[b] | 0.52% | 0.50% | 0.50% |
| MEA 99%[c] | 2.09% | 2.40% | 2.42% |
| KOH 46% | 0.18% | 0.16% | 0.22% |
| Palm seed fatty acid[d] | 0.00% | 11.38% | 0.00% |
| Coco fatty acid[e] | 11.75% | 0.00% | 11.36% |
| Grape seed oil[f] | 14.28% | 13.82% | 13.82% |
| Turkish red oil[g] | 2.27% | 2.24% | 2.15% |
| Parabene premix[h] | 0.74% | 0.73% | 0.72% |
| Tegobetain F50[i] | 5.58% | 5.36% | 5.29% |
| Meadowfoam seed oil[j] | 2.30% | 4.47% | 4.50% |
| Lutensol TO3[k] | 0.78% | 0.69% | 0.72% |
| SUM: | 100.00% | 100.00% | 100.00% |
| pH: | 7.277 | 7.699 | 7.769 |
| Acid value | 38.03 | 36.37 | 36.00 |
| Viscosity[l] | 4900 cp | 3330 cp | 18600 cp |
| pH[m]/acid value | 7.277 | 7.699 | 7.769 |
| Stability Test |  |  |  |
| Acid value | 38.03 | 36.37 | 36.00 |
| Day 1 |  |  |  |
| −5° C./20° C. | 1/1 | 1/1 | 1/1 |
| 37° C./50° C. | 1/1 | 1/1 | 1/1 |
| Day 7 |  |  |  |
| −5° C./20° C. | 1/1 | 1/1 | 1/1 |
| 37° C./50° C. | 1/1 | 1/1 | 1/1 |
| Day 30 |  |  |  |
| −5° C./20° C. | 1/1 |  |  |
| 37° C./50° C. | 0/2 |  |  |

-continued

Day 60

−5° C./20° C.
37° C./50° C.
Day 180

−5° C./20° C.
37° C./50° C.

| Raw material | JL-30 % | Raw material | JL-57-C % |
|---|---|---|---|
| Water, cold | 57.28 | Water, cold | 56.97 |
| EDTA 40% | 0.31 | Citric acid | 0.49 |
| Citric acid | 0.49 | MEA 99% | 2.17 |
| MEA 99% | 2.27 | KOH 46% | 0.17 |
|  | 0.00 | EDTA 40% | 0.00 |
| KOH 46% | 0.15 |  | 0.00 |
| Palm kernel fatty acid | 11.24 | Palm kernel fatty acid | 11.24 |
|  | 0.00 | Meadowfoam seed | 4.39 |
| Grape seed oil | 13.65 | Grape seed oil | 13.58 |
| Turkish red oil | 2.18 | Turkish red oil | 2.19 |
| Phenonip | 0.66 |  | 0.00 |
| Tegobetaine F50 | 5.29 | Tegobetaine F50 | 5.30% |
| Meadowfoam seed | 4.44 |  |  |
|  | 0.00 |  | 0.00 |
|  | 0.00 | Sepacide HB2 | 0.77 |
|  | 0.00 | Nipabutyl sodium | 0.19 |
|  | 0.00 | NaHMF | 0.50 |
| Rilanit GRMO | 2.03 | Rilanit GRMO | 2.04 |
| SUM: | 100.00 | SUM: | 100.00 |
| pH: | 7.559 | pH: | 7.384 |
| Visc. 6/10: | 2230 cp | Visc. 6/10 | 2520 cp |
| Acid value | 37.61 | Acid value | 34.30 |

| Stability/Name | JL-30 | JL-57-C |
|---|---|---|
| Viscosity | 2230 cp | 2520 cp |
| pH/acid No. | 7.559 | 7.384 |
| Mf./ref. % |  |  |
| Special | Acid value 37.61 | Acid value 34.30 |
| Day 1 |  |  |
| −5° C./20° C. | 1/1 | 1/1 |
| 37° C./50° C. | 1/1 | 1/1 |
| Day 7 |  |  |
| −5° C./20° C. | 1/1 | 1/1 |
| 37° C./50° C. | 1/1 | 1/1 |
| Day 30 |  |  |
| −5° C./20° C. | 1/1 | 1/1 |
| 37° C./50° C. | 1/1 | 1/2 |
| Day 60 |  |  |
| −5° C./20° C. | 1/1 |  |
| 37° C./50° C. | 0/1 |  |
| Day 180 |  |  |
| −5° C./20° C. | 1/1 |  |
| 37° C./50° C. | 0/0 |  |

[a] chelating agent
[b] stabilizing agent with respect to oxidation
[c] monoethanolamine (part of the surfactant/emulsifier formed)
[d,e,f] def part of the oily phase
[g] co-surfactant/co-emulsifier
[h] preservative mixture of parabens
[i] co-surfactant/co-emulsifier (amphotheric substance)
[j] lipid with good adherence to the skin
[k] co-surfactant/co-emulsifier
[l] the apparent viscosity determined with a Brookfield Rheometer at 20° C.; the viscosity is aimed at being in a range of about 500–5,000 cp such as about 1,000–4,000 cp, about 2,000–5,000 cp or about 3,000–4,000 cp
[m] pH is aimed at being in a range of about 7–8.5 such as about 7.7–7.9

Example 3

Oxidative Stability of a Cleansing Lotion According to the Invention

The oxidative stability of a sample of Batch JL-25 (see Example 2) was tested at Aarhus Olie, Aarhus, Denmark employing an Oxipress running at 80° C. The results show that the sample is stable for about 31–32 hours. Then, the oxidation process stats and the stability decreases evenly.

Further tests have shown that substituting the fatty acids derived from grape seed oil with fatty acids derived from glyceroltricaprylate/caprate or with CREMEOL PS6 results in a much higher stability of the cleansing lotion.

Example 4

Examination of the Ecotoxicity of a Cleansing Lotion According to the Invention

According to e.g. the National Swedish Nature Conservancy Board (pubpl SNV 1975:10) only degreasing agents should be used which at loading tests according to IVL method 2 gives a mineral oil content of 100 mg/l or lower after 2 hours.

Testing according to the ST method of PLUM Washing lotion gives a mineral oil content of <10 mg/l and the content is of the same order of magnitude compared with results obtained after testing of a blank containing plain water.

Example 5

Determination of the Fatty Acid Content in the Aqueous Phase and the Oily Phase, Respectively, after Flushing with a Liquid An accurate amount of a lotion according to the invention is applied to wet hands and the hands are washed thoroughly for two minutes. The hands are then rinsed by flushing with 10 l of tap water having a hardness degree in the range of 5–30 degrees. The rinsing water is collected and allowed to stand for 0.5 hour in order to secure a complete separation into two phases (the separation takes place substantially immediately upon flushing). The two layers are separated and the acid values of the oily phase and of the aqueous layer, respectively, are determined.

The results show that free fatty acids are predominantly present in the aqueous phase indicating that the emulgating properties of a fatty acid based surfactant/emulsifier is destroyed during rinsing. Furthermore, the results indicate that the surfactant/emulsifier is substantially completely washed off the hands during the rinsing period.

Example 6

Investigation of the Cleansing Effect of a Lotion According to the Invention and of the Effect on the Skin An oil-in-water emulsion in the form of a lotion and having the composition stated below was tested in vivo on workers at Slagteriskolen, Roskilde, Denmark.

| Ingredients | JL-28 w/w |
|---|---|
| Water, cold, purified | 57.94% |
| EDTA 40%[a] | 0.31% |
| Citric acid[b] | 0.50% |
| MEA 99%[c] | 2.40% |
| KOH 46% | 0.16% |
| Palm seed fatty acid[d] | 11.38% |
| Glycerol tricaprylate/caprate[f] | 13.82% |
| Turkish red oil[g] | 2.24% |
| Parabene premix[h] | 0.73% |
| Tegobetain F50[i] | 5.36% |
| Meadowfoam seed oil[j] | 4.47% |
| Lutensol TO3[k] | 0.69% |
| SUM: | 100.00% |

The following washing instructions were given:

Wash after work

Purpose:

To loosen and wash off microorganisms

Product:

Plum Cleansing lotion

Instructions for use:

Flush hands with water. Apply one squeeze of lotion.

Work lotion thoroughly with hands for 20 seconds. Add water, rinse and dry hands.

The evaluation of the acceptance and effect of the cleansing lotion according to the invention is based on the following questionnaire and on personal interviews with the users (see below).

Furthermore, the evaluation is based on determination of TEWL, capacitance and elasticity as described above.

Questionnaire for Plum Cleansing lotion

How does it feel to wash with the product?
Pleasant    Good    Not so good    Unpleasant
How is the cleansing effect?
Outstanding    Good    Not so good    Poor
Was the product easy to rinse off?
Yes    No
What effect does the product have after it has been rinsed off compared to the soap you are using today?
Less desiccating    The same    More desiccating
Do you have dry hands already?
Yes    No
What do you think of the product - overall?
Good    Poor Own comments:

Evaluation of liquid soap/cleansing lotion/96—personal interviews

Grades: 1–5, 1=good 5=poor or comments

Product: LJ-19 Person evaluating:

| Grade | 1 | 2 | 3 | 4 | 5 | Comments ? |
|---|---|---|---|---|---|---|
| Immediately felt effect of the product | | | | | | |
| Ability to spread on wet hands | | | | | | |
| Foamablity in wet washing | | | | | | |
| Rinsing characteristics | | | | | | |
| Effect felt on skin immediately after washing | | | | | | |
| Effect felt on skin immediately after drying | | | | | | |
| Effect felt on skin five minutes later | | | | | | |
| Comments, if any | | | | | | |

Results

The following general points should be noted from the answers obtained at the slaughterhouse:

The foaming property of the product is relatively low compared to that of normal soap. The users who can accept this fact express that their immediate impression of the product is good, that it is easy to spread and dilute on the skin, and that it is easy to rinse off. The cleansing effect is good and even if there is a lot of grease on the skin, this is easily washed off—at least as easily as when using a strong soap. Immediately after washing and later, the experience of the hands is rated high: as average—and mainly above.

In particular those persons working with areas involving a lot of water or a humid environment and who have a tendency to have dry skin, normally have a high preference for such a product that really brings back fat to the skin in connection with the washing process.

A survey at four hospitals—79 responses—(with a slightly different questionnaire) clearly showed that many of the employees with a tendency to have dry skin preferred washing lotion over an liquid soap of good quality.

Example 7

Comparative Testing of POLO SPORT WOMAN® by RALPH LAURENS and a Cleansing Lotion According to the Invention As mentioned on the package of POLO SPORT WOMAN® 200 ml it contains the following ingredients:

water, sodium laureth sulfate, Meadowfoam seed oil, sorbitan monoisostearate, PEG-6 caprylic/capric glycerides, fragrance, glycerin, cocamide MEA, muristic acid, disodium cocoamphodiacetate, sea fennel, extract, sea rocket extract, pacific sea kelp extract, algae extract, tocopherol acetate, propylene glycol, cocamidopropyl betaine, phenoxyethanol, guar hydroxypropyltrimonium chloride, methylparaben, propylparaben, disodium EDTA. No specific composition is given and, therefore, in order to document that this composition from Ralph Laurens is different from a composition according to the present invention, the Ralph Laurens washing product and a composition according to the invention have been subjected to the tests given in the following.

The washing product according to the invention had the composition given in Example 2 under the heading "JL-30" (in this example also denoted PLUM Washing lotion):

Tests performed:

i) TEWL (transepidermal water loss) has been performed using the antecubital fossa (flex area of elbow). The antecubital fossa is especially suited to washing tests because the skin is thin and elastic and contains stratum corneum as well as stratum lucidum. Furthermore, due to the inventors' experience a washing test using the antecubital fossa gives very good and reproducible results for a fairly large area of the skin. In particular a good reproducibility is observed with regard to TEWL.

ii) Determination of sebum content before and after the washing procedures by means of a Sebumeter iii) Measurement of the skin moisture by means of a Corneometer
iv) Separation test of the compositions after dilution with tap water having the following composition:

| Test | Result |
|---|---|
| pH | 7.8 |
| Conductivity | 75 mS/m |
| Permanganat value KMnO4 | 2.8 mg/l |
| Evaporation residue | 470 mg/l |
| Calcium | 120 mg/l |
| Magnesium | 10 mg/l |
| Hardness, total | 18.9 degrees dH |
| Sodium | 26 mg/l |
| Potassium | 2.7 mg/l |
| Ammoniak + ammonium | 0.01 mg/l |
| Iron | 0.005 mg/l |
| Mangan | 0.01 mg/l |
| Hydrocarbonate | 320 mg/l |
| Chloride | 45 mg/l |
| Sulfate | 65 mg/l |
| Nitrate | 1 mg/l |
| Nitrite | 0.005 mg/l |
| Phosphor, total-P | 0.02 mg/l |
| Fluoride | 0.22 mg/l |
| Oxygen content | 7 mg/l |
| Carbondioxide, aggr. | 2 mg/l |
| Nickel | 1.8 microg/l |

The elbow washing test is performed using two different products; one for the right and one for the left elbow.

Applied procedure:

The antecubital fossa is rinsed/wetted under running aqua communes (water analysis, se above) of a temperature of approx. 20° C. Then 1 g of washing product is added. The washing product is worked with the second and third finger of the other hand in soft circular movements for 20 sec over an area of approx. 20 cm$^2$. Next, running water is added under continuous working, and the product is thoroughly rinsed off with the running water of 20° C. The washing process is completed after 30–35 sec. Afterwards, soft cloth is used for dabbing.

Measurements of the skin are undertaken before the first washing, after 10th, 20th and 40th washing. All skin measurements are performed on conditioned skin—after a pause of at least 30 min.

Previous experiences:

When using an ordinary liquid soap, no lipid or nearly no lipid will measure on the skin (Sebumeter) Measuring value: 0.

Provided that prior to washing TEWL is approx. 11, the TEWL after 20 washings will increase to 13–18 when using an ordinary liquid soap.

However, as is seen from the results below, TEWL does not increase in the case of PLUM Washing lotion.

| | Comparative measurements | |
|---|---|---|
| Item | Left bend of arm POLO SPORT WOMAN ® | Right bend of arm PLUM Washing lotion |
| Before washing | | |
| TEWL | 11.3 | 11.3 g/m$^2$h |
| Sebumeter | 2 | 2 |
| Corneometer | 60–90 | 60–95 |
| After 10 washings | | |
| TEWL | 11,8 | 10 |
| Sebumeter | 0 | 3 |

| | Comparative measurements | |
|---|---|---|
| Item | Left bend of arm POLO SPORT WOMAN ® | Right bend of arm PLUM Washing lotion |
| Corneometer | 65–90 | 65–90 |
| After 20 washings | | |
| TEWL | 11.3 | 11 |
| Sebumeter | 0 | 4 |
| Corneometer | 60–85 | 55–85 |
| After 40 washings | | |
| TEWL | 14 | 10 |
| Sebumeter | 1 | 6 |
| Corneometer | 55–85 | 60–85 |

The above measurements clearly demonstrate that PLUM Washing lotion leaves the lipid on the skin in a considerable amount—approx. an amount equalling the natural amount of lipid on the skin.

Comparing these test results to the results of separation tests for washing lotions clearly demonstrates that the ability of PLUM Washing lotion to separate the oil in a 1% solution (the normal water dilution in a washing process where water consumption is sparse) also in practice is demonstrated by the fact that lipid is left on the skin.

Results of Separation Test

1% w/w dilution (1 g of washing product is diluted to 100 g with aqua communis having a hardness degree of about 18 degrees)

| | POLO SPORT WOMAN ® | PLUM Washing lotion |
|---|---|---|
| after 1 min. | homogenous | separated |
| after 1 hour | homogenous | separated |
| after 4 hours | homogenous | separated |
| after 24 hours | homogenous | separated |

Upon dilution with distilled water, all corresponding 1% dilutions remained stable for 24 hours.

In conclusion, the washing product POLO SPORT WOMAN® does not fulfil the requirements claimed in connection with the present invention and, furthermore, its ability to leave lipid on the skin is decreased compared with PLUM Washing lotion.

Example 8

Separation Tests of POLO SPORT WOMAN® and PLUM Washing Lotion

In the following results are given from separation and stirring tests of the washing products from Example 7. From the results it is clear that PLUM Washing lotion quickly separates into two distinct phases when diluted with plain water, i.e. water having a degree of hardness of from about 8 to about 25 degrees, and when a dilution with water of the washing product is 1 g of the washing product to a total of 100 g, i.e. a dilution which is relevant for practical use. In contrast, POLO SPORT WOMAN® does not separate under these conditions.

Moreover, it is seen that when distilled water is used, no separation occurs within 24 hours. These results support that ions like $Ca^{2+}$ and $Mg^{2+}$ present in plain water play an important role in the separation process.

Based on the results given below and the results given in the Examples above, it is concluded that PLUM Washing lotion has unique properties with respect to its ability of separate into an oily and an aqueous phase and, thus, it enables a part of the oily phase to remain on the skin or wherever it is applied (e.g. on the hair) while maintaining its cleansing effect.

|  | POLO SPORT WOMAN ® | PLUM Washing lotion |
|---|---|---|
| Test No. 5A/7A |  |  |
| Concentration | 1% | 1% |
| Diluted with | plain water | plain water |
| Visually inspected after; |  |  |
| 5 min | homogenous | separated with white cream 2 mm |
| 15 min | homogenous | separated with white cream 2 mm |
| 30 min | homogenous | separated with white cream 2 mm |
| 60 min | homogenous | separated with white cream 2 mm |
| Test No. 5B/7B |  |  |
| Concentration | 1% | 1% |
| Diluted with | plain water | plain water |
| Visually inspected after; |  |  |
| 5 min | homogenous | separated with white cream 2 mm |
| 15 min | homogenous | separated with white cream 2 mm |
| 30 min | homogenous | separated with white cream 2 mm |
| 60 min | homogenous | separated with white cream 2 mm |
| Test No. 6A/8A |  |  |
| Concentration | 1% | 1% |
| Diluted with | distilled water | distilled water |
| Visually inspected after; |  |  |
| 5 min | homogenous | homogenous |
| 15 min | homogenous | homogenous |
| 30 min | homogenous | homogenous |
| 60 min | homogenous | homogenous |
| Test No. 6B/8B |  |  |
| Concentration |  |  |
| Diluted with | distilled water | distilled water |
| Visually inspected after; |  |  |
| 5 min | homogenous | homogenous |
| 15 min | hornogenous | homogenous |
| 30 min | homogenous | homogenous |
| 60 min | homogenous | homogenous |

| Viscosity determination of JL-30 | | | | | | |
|---|---|---|---|---|---|---|
| Speed RPM | Torque % | Viscosity cP | Shear Stress D/Cm$^2$ | Shear Rate 1/sec | Temperature °C. | Time sec |
| 0.1 | 0.9 | 17694.0 | 35.4 | 0.20 | 20.1 | 22.0 |
| 0.2 | 1.0 | 9830.0 | 39.3 | 0.40 | 20.1 | 20.5 |
| 0.3 | 1.2 | 7864.0 | 47.2 | 0.60 | 20.2 | 20.9 |
| 0.5 | 1.4 | 5504.8 | 55.0 | 1.00 | 20.1 | 20.6 |
| 1.0 | 1.8 | 3538.8 | 70.8 | 2.00 | 20.1 | 20.6 |
| 1.5 | 2.1 | 2752.4 | 82.6 | 3.00 | 20.1 | 20.6 |
| 2.0 | 2.4 | 2359.2 | 94.4 | 4.00 | 20.1 | 20.6 |
| 2.5 | 2.7 | 2123.3 | 106.2 | 5.00 | 20.1 | 20.6 |
| 3.0 | 2.9 | 1900.5 | 114.0 | 6.00 | 20.1 | 20.6 |

Example 9

Cleansing Test of Plum Washing Lotion and POLO SPORT WOMAN®

The above products' cleansing properties were tested on a standard of dirt (thin). The plates were covered with a standard of dirt and left to dry for four weeks at 30° C. A standard of dirt consists of 1% carbon black in the mineral motor oil Shell Super.

The test was carried out as follows:
1. 1.5 g of cleansing product was added and spread on to the plate
2. Light washing with a brush for 30 sec. following which luke warm water was added, and then washing with a brush was continued again for 30 sec.
3. The plate was left to dry
4. Evaluation of the results.

| Name | Special | Score solubility | Score rinsability | Other |
|---|---|---|---|---|
| Plum Washing lotion | tube | 2.0 | 2.0 |  |
| POLO SPORT WOMAN ® | std. | 3.0 | 3.0 |  |

Scores given between 1 and 5 where 1 corresponds to a very fine cleansing effect and 5 to an unacceptable cleansing effect.

Example 10

Effect of Plum Washing Lotion Against Lice

Human clothing lice, *Pediculus humanus,* were obtained from the culture colony maintained by the Medical Entomology Centre. Adult lice used in the test were mixed male and females that were fed not less than four hours before exposure to the test product. The resting period after feeding is allowed to permit the insects to excrete fluid from their blood meal and reduce mortality from handling.

Adult lice were counted into three replicate batches of twenty-one for each test, allowing for any that may be lost through washing. The lice were provided with a gauze substrate to stand on during the tests.

For the test the lice were exposed to the product mimicking as closely as possible use by consumers as follows;

The lice were washed with a 1:15 solution Plum Washing lotion and then exposed to the experimental formulation for 10 minutes, during which the gauze was turned over to ensure even coverage. They were then washed and rinsed in a 1:15 solution of Plum Washing lotion and three changes of tap water (35° C.) twice before being blotted dry, using a medical wipe tissue and incubated under normal maintenance conditions until the results were recorded after 24 hours.

What is claimed is:

1. An oil-in-water emulsion for application on a skin surface, the emulsion comprising an oily phase and an aqueous phase, said oily phase comprising a first lipid of vegetable or animal origin, the emulsion being stabilized by containing at least one surfactant/emulsifier, the at least one surfactant/emulsifier being substantially removed from a skin surface onto which the emulsion has been applied and from the emulsion by flushing with liquid, thereby leaving at least a part of the oily phase on the skin, and the emulsion when diluted with tap water having a degree of hardness of about 18 degrees in a volume of 100 parts of water to one part of the emulsion at ambient temperature, being separated into at least two distinct phases after standing for 24 hours at ambient temperature, wherein the oil-in-water emulsion has a pH value of at least 6, and at least about 50% w/w of the total concentration of the at least one surfactant/emulsifier which is a fatty acid derivative, wherein said derivative has a fatty acid component which is a saturated or unsaturated $C_{10}$–$C_{24}$ hydrocarbon carboxylic acid or mixtures thereof.

2. An emulsion according to claim 1, wherein the emulsion comprises at least 1% w/w of the first lipid which has good adherence to the skin.

3. An emulsion according to claim 2, wherein the first lipid is a lipid which has such a water retention ability that 1 g of the lipid can retain at least 2 g of water at ambient temperature.

4. An emulsion according to claim 3, wherein the first lipid is selected from the group consisting of Meadowfoam seed oil, shea butter (Karite butter), cocoa butter, lanolin, and mixtures thereof.

5. An emulsion according to claim 2, wherein the first lipid is a triglyceride comprising at least 90% of long chain $C_{20}$–$C_{22}$ fatty acids.

6. An emulsion according to claim 5, wherein the triglyceride comprises a combination of a monoenoic and a dienoic fatty acid component, the ratio of the monoenoic fatty acid component to the dienonic fatty acid component being in a range corresponding to from about 1:99 to about 99:1 and the two unsaturated bonds of the dienoic fatty acid component being spaced from each other by at least 5 carbon atoms.

7. An emulsion according to claim 5, wherein the triglyceride is Meadowfoam seed oil.

8. A emulsion of claim 1 wherein the at least one surfactant/emulsifier is a fatty acid derivative selected from the group consisting of sodium salts, potassium salts, ammonium salts, substituted ammonium salts, unsubstituted amides, amides with substituted amines, monoethanolamides, diethanolamides, triethanolamides, propanolamines, and isopropanolamines, and mixtures thereof.

9. An emulsion of claim 1 wherein the fatty acid component is selected from the group consisting of capric acid ($C_{10}H_{20}O_2$), undecylenic acid ($C_{11}H_{22}O_2$) lauric acid ($C_{12}H_{24}O_2$), myristic acid ($C_{14}H_{28}O_2$), palmitic acid ($C_1H_{32}O_2$), stearic acid ($C_{18}H_{30}O_2$), arachidie acid ($C_{20}H_{40}O_2$), behenic acid ($C_{22}H_{44}O_2$), and lignoceric acid ($C_{24}H_{48}O_2$), and mixture, thereof.

10. An emulsion of claim 1 wherein the fatty acid component is selected from the group consisting of palmitolcic acid ($C_{16}H_{20}O_2$), olcic acid ($C_{18}H_{34}O_2$), claidic acid ($C_{18}H_{34}O_2$), crucic acid ($C_{22}H_{42}O_2$), and brassidic acid ($C_{22}H_{42}O_2$), and mixtures thereof.

11. An emulsion of claim 1 further comprising an additional surfactant/emulsifier having an HLB value of from about 4 to about 30.

12. An emulsion of claim 1 wherein the total concentration of surfactant/emulsifier in the emulsion is from about 10 to about 35 % w/w.

13. An emulsion of claim 1 wherein the acid value of the emulsion is in a range of from about 25 to about 45.

14. An emulsion of claim 1 wherein the pH of the emulsion is from about 7.0 to about 8.0.

15. An emulsion of claim 1 wherein the pH of the emulsion is from about 7.2 to about 7.8.

16. An emulsion of claim 1 wherein the oily phase comprises a second lipid selected from vegetable fats and animal fats.

17. An emulsion of claim 1 wherein the oily phase comprises a second lipid that is a vegetable fat selected from the group consisting of avocado oil, coconut fat, cocoa butter, rapeseed oil, maize oil, sesame oil, olive oil, soybean oil, palm oil, grape seed oil, almond oil, linseed oil, peanut oil, walnut oil, tall oil, thistle seed oil, wheat germ oil, sunflower oil, poppy seed oil, cottonseed oil, persic oil, apricot oil, jojoba oil, castor oil, hydrogenated vegetable oils, CREMEOL PS 6, POS, and PSW, and mixtures thereof.

18. An emulsion of claim 1 wherein the oily phase comprises a second lipid that is a vegetable fat derived from plant species from the family Limnanthaceue.

19. An emulsion of claim 1 wherein the oily phase comprises a second lipid that is a vegetable fat derived from plant species of *Limnathes alba.*

20. An emulsion of claim 1 wherein the oily phase comprises a second lipid selected from mono-, di- and triglycerides.

21. An emulsion of claim 1 further comprising a drug.

22. An emulsion of claim 21 wherein the drug is a vitamin.

23. An emulsion of claim 1 wherein the oily phase comprises meadowfoam seed oil and Karite butter extract or Karite extract.

24. An emulsion of claim 2 wherein the first lipid is mixed with an extract selected from the group consisting of Kante butter extract, karite extract, aloe barbadensis extract, apricot extract, arnica montana extract, balm mint extract, bamboo extract, bearberry extract, beet extract, bilberry extract, birch leaf extract, blackberry leaf extract, bladderwrack extract, buckwheat extract, burdock extract, butcher-broom extract, calendula extract, carrot extract, matricaria extract, cherinmoya extract, jujube extract, coltsfoot extract, comfroy extract, coneflower extract, balsam copaiba, cornflower extract, cucumber extract, dog rose hips extract, fennel extract, ginger extract, ginkgo extract, ginseng extract, camellia sinensis extract, guarana extract, cratacgus monogina extract, hayflower extract, henna extract, hops extract, horsetail extract, horsechesnut extract, hydrocotylextract, ivy extract, Job's tears extract, juniperus communis extract, kiwi extract, lady's mantle extract, laminaria digitata extract, lavender extract, lemon peel extract, licorice extract, linden extract, lithospermum officinale extract, mallow extract, mango extract, marshmallow extract, melon extract, mimosa tenuiflora bark extract, white oak bark extract, English oak extract, oyster shell extract, pansy extract, peach extract, capsicum frutescens oleoresin, capsicu frutescens extract, peppermint extract, quillaja saponaria extract, raspberry extract, krameria triandra extract, rosemary extract, sage extract, St. John's wort extract, stinging nettle extract, strawberry extract, soapwort extract, thyme extract, walnut extract, watercress extract, wheat germ extract, willow bark extract, and witch hazel extract.

25. A method for cleansing or conditioning a skirt surface, comprising applying, to the skin surface, the oil-in-water emulsion of claim 1, and flushing the skin surface with a liquid, whereby the at least one surfactant/emulsifier is substantially removed from the skin surface onto which the emulsion has been applied and thereby leaving at least part of the oily phase on the skin.

26. A method for treating human skin comprising applying, to tho skin surface, the oil-in-water emulsion of claim 1, and flushing the skin surface with a liquid, whereby the at least one surfactant/emulsifier is substantially removed from the skin surface onto which the emulsion has been applied and thereby leaving at least part of the oily phase on the skin, said treating decreasing transepidermal water loss as compared with transepidermal loss measured immediately before initiation of the treating.

27. A method for treating mammals against parasites belonging to the phylum Arthropoda, the method comprising applying to skin of a mammal suffering therefrom an effective amount of an oil-in-water according, to claim 1.

28. A method for protection of human skin against the sun, the method comprising applying to the human skin a protective effective amount of an oil-in-water emulsion according to claim 1.

29. An emulsion according to claim 1 further comprising an active agent selected from disinfectants, antiseptics and drug substances.

30. An emulsion according to claim 29 comprising an active agent selected from disinfectants and antiseptics.

31. An emulsion according to claim 29 wherein the active agent is a drug substance.

32. An emulsion according to claim 1 further comprising a substance selected from sunscreens, UV absorbers, insect repellants, and anti-parasitic agents.

* * * * *